US007763856B2

(12) United States Patent
Kiesel et al.

(10) Patent No.: US 7,763,856 B2
(45) Date of Patent: Jul. 27, 2010

(54) PRODUCING TIME VARIATION IN EMANATING LIGHT

(75) Inventors: Peter Kiesel, Palo Alto, CA (US); Markus Beck, Palo Alto, CA (US); Michael Bassler, Menlo Park, CA (US); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 12/023,436

(22) Filed: Jan. 31, 2008

(65) Prior Publication Data

US 2009/0194705 A1  Aug. 6, 2009

(51) Int. Cl.
*G01N 21/85* (2006.01)
*G01N 21/63* (2006.01)

(52) U.S. Cl. .............. 250/343; 250/373; 250/564; 250/428; 250/432 R; 250/437

(58) Field of Classification Search ............ 250/288, 250/343, 364, 373, 564, 428, 432 R, 437, 250/432, 458.1; 422/82.08, 82.05
See application file for complete search history.

(56) References Cited

U.S. PATENT DOCUMENTS

| 4,455,089 A | | 6/1984 | Yeung et al. |
| 4,573,796 A | * | 3/1986 | Martin et al. ............ 356/318 |
| 5,151,585 A | | 9/1992 | Siebert |
| 5,243,614 A | | 9/1993 | Wakata et al. |

(Continued)

FOREIGN PATENT DOCUMENTS

| WO | WO 95/20144 A1 | 7/1995 |
| WO | WO 02/25269 A2 | 3/2002 |

OTHER PUBLICATIONS

Bassler, ., Schmidt, O., Kiesel, P., Johnson, N.M., "Class Identification of Bio-Molecules Based on Multi-Color Native Fluorescence Spectroscopy", International Journal of High Speed Electronics and Systems (IJHSES), vol. 17, Issue 4, 2007, pp. 671-680.

(Continued)

*Primary Examiner*—David P Porta
*Assistant Examiner*—Yara B Green
(74) *Attorney, Agent, or Firm*—Mark W. Hrozenchik; Leading-Edge Law Group, PLC

(57) ABSTRACT

An excitation component or arrangement can provide excitation to a moving object so that information is encoded in time variation of light emanating from the object. For example, in each of a sequence of segments, it can provide a respective non-binary excitation spectrum, and the spectra can be different with a non-interference-like transition between them; because the object emanates light differently in response to the different spectra, photosensing results can be obtained that include encoded information about the object. The non-binary spectra could be different intermediate intensities, such as different gray levels or different intensities of one color or could be different colors. The excitation can be provided in a pattern with non-interference-like transitions between regions, and object motion can also be controlled. In another approach, a trigger signal can cause a time-varying excitation in a region, with non-interference-like transitions between intervals of excitation, such as black/white, multiple colors, or gray levels.

33 Claims, 16 Drawing Sheets

U.S. PATENT DOCUMENTS

| | | | |
|---|---|---|---|
| 5,312,535 | A | 5/1994 | Waska et al. |
| 5,324,401 | A | 6/1994 | Yeung et al. |
| 5,370,842 | A | 12/1994 | Miyazaki et al. |
| 5,437,840 | A | 8/1995 | King et al. |
| 5,445,934 | A | 8/1995 | Fodor et al. |
| 5,682,038 | A | 10/1997 | Hoffman |
| 5,760,900 | A * | 6/1998 | Ito et al. ..................... 356/338 |
| 5,798,222 | A | 8/1998 | Goix |
| 5,880,474 | A | 3/1999 | Norton et al. |
| 5,982,478 | A | 11/1999 | Ainsworth et al. |
| 6,429,022 | B1 | 8/2002 | Kunz et al. |
| 6,558,945 | B1 | 5/2003 | Kao |
| 6,795,190 | B1 | 9/2004 | Paul et al. |
| 6,816,257 | B2 | 11/2004 | Goix |
| 6,839,140 | B1 | 1/2005 | O'Keefe et al. |
| 6,865,198 | B2 | 3/2005 | Taubman |
| 6,867,420 | B2 | 3/2005 | Mathies et al. |
| 6,906,792 | B2 | 6/2005 | Ortyn et al. |
| 7,034,933 | B2 | 4/2006 | Walker et al. |
| 7,248,361 | B2 | 7/2007 | Kiesel et al. |
| 7,268,868 | B2 | 9/2007 | Kiesel et al. |
| 7,277,569 | B2 | 10/2007 | Bruce et al. |
| 7,291,824 | B2 | 11/2007 | Kiesel et al. |
| 7,305,112 | B2 | 12/2007 | Curry et al. |
| 7,433,552 | B2 | 10/2008 | Kiesel et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,522,786 | B2 | 4/2009 | Kiesel et al. |
| 7,545,513 | B2 | 6/2009 | Kiesel et al. |
| 7,547,904 | B2 | 6/2009 | Schmidt et al. |
| 7,554,673 | B2 | 6/2009 | Kiesel et al. |
| 7,701,580 | B2 | 4/2010 | Bassler et al. |
| 2003/0020915 | A1 | 1/2003 | Schueller et al. |
| 2003/0235924 | A1* | 12/2003 | Adams et al. ............... 436/172 |
| 2004/0038386 | A1 | 2/2004 | Zesch et al. |
| 2004/0067167 | A1 | 4/2004 | Zhang et al. |
| 2005/0128479 | A1 | 6/2005 | Gilbert et al. |
| 2005/0162648 | A1* | 7/2005 | Auer et al. .................. 356/318 |
| 2005/0213082 | A1 | 9/2005 | DiBernardo et al. |
| 2006/0203224 | A1 | 9/2006 | Sebastian et al. |
| 2006/0268260 | A1 | 11/2006 | Liu et al. |
| 2006/0274313 | A1 | 12/2006 | Gilbert et al. |
| 2007/0070347 | A1 | 3/2007 | Scherer et al. |
| 2007/0076210 | A1 | 4/2007 | Kiesel et al. |
| 2007/0145236 | A1* | 6/2007 | Kiesel et al. ............. 250/208.1 |
| 2007/0145249 | A1 | 6/2007 | Kiesel et al. |
| 2007/0146704 | A1 | 6/2007 | Schmidt et al. |
| 2007/0147189 | A1 | 6/2007 | Schmidt et al. |
| 2007/0147728 | A1 | 6/2007 | Schmidt et al. |
| 2008/0013092 | A1 | 1/2008 | Maltezos et al. |
| 2008/0013877 | A1 | 1/2008 | Schmidt et al. |
| 2008/0181827 | A1* | 7/2008 | Bassler et al. ............... 422/119 |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186494 | A1 | 8/2008 | Kiesel et al. |
| 2008/0186504 | A1 | 8/2008 | Kiesel et al. |
| 2008/0186508 | A1 | 8/2008 | Kiesel et al. |
| 2008/0187011 | A1 | 8/2008 | Kiesel et al. |
| 2009/0190121 | A1 | 7/2009 | Hegyi et al. |
| 2009/0195773 | A1 | 8/2009 | Bassler et al. |
| 2009/0195852 | A1 | 8/2009 | Bassler et al. |
| 2009/0220189 | A1 | 9/2009 | Kiesel et al. |

OTHER PUBLICATIONS

"Flow Cytometry", printed from www.wellscenter.iupui.edu/MMIA on Jan. 29, 2008, 4 pages.

Bhatta, H., Goldys, E.M., and Learmonth, R., "Rapid Identification of Microorganisms by Intrinsic Fluorescence", Proc. of SPIE, vol. 5699, 2005, pp. 9-18.

Singh, K., Liu, C., Capjack, C., Rozmus, W., and Backhouse, C.J., "Analysis of cellular structure by light scattering measurements in a new cytometer design based on a liquid-core waveguide", IEE Proc.-Nanobiotechnol., vol. 151, No. 1, Feb. 2004, pp. 10-16.

Liang, X.J., Liu, A.Q., Zhang, X.M., Yap, P.H., Ayi, T.C., and Yoon, H.S., "Refractive Index Measurement of Single Living Cell Using a Biophotonic Chip for Cancer Diagnosis Applications", 9th International Conference on Miniaturized Systems for Chemistry and Life Sciences, Oct. 9-13, 2005, pp. 464-466.

Stanford Research Systems, "Optical Chopper-SR540-Optical Chopper System", printed from thinkSRS.com website on Oct. 21, 2008, 2 pg.

Office communication in U.S. Appl. No. 12/024,490, mailed Dec. 24, 2008, 12 pages.

Shapiro, H. M., Practical Flow Cytometry, Fourth Edition, Wiley-Liss, 2003, Table of Contents and pp. 49-59, 124-183, 191-197, 345, and 364-366.

Hoffman, R. A., "Flow Cytometry: Instrumentation, Applications, Future Trends and Limitations", Springer Series on Fluorescence, vol. 6, 2008, pp. 307-342.

Office communication in U.S. Appl. No. 11/702,470, mailed Apr. 25, 2008, 22 pages, published in PAIR.

Amendment in U.S. Appl. No. 11/702,470, submitted Jul. 25, 2008, 21 pages, published in PAIR.

Office communication in U.S. Appl. No. 11/702,470, mailed Oct. 31, 2008, 22 pages, published in PAIR.

Amendment in U.S. Appl. No. 11/702,470, submitted Jan. 30, 2009, 22 pages, published in PAIR.

Notice of Allowance and Fee(s) Due in U.S. Appl. No. 11/702,470, mailed Apr. 24, 2009, 15 pages, published in PAIR.

Amendment in U.S. Appl. No. 12/024,490, submitted Mar. 24, 2009, 32 pages.

Office communication in U.S. Appl. No. 12/022,485, mailed Jan. 16, 2009, 18 pages.

Amendment in U.S. Appl. No. 12/022,485, submitted Apr. 15, 2009, 30 pages.

Bracewell, R. N., The Fourier Transform and Its Applications, Second Edition, McGraw-Hill, 1978, Table of Contents and pp. 24-50, 98-126, and 177-188.

Office communication in U.S. Appl. No. 12/022,485, mailed Jul. 31, 2009, 5 pages, published in PAIR.

Response to Restriction Requirement in U.S. Appl. No. 12/022,485, submitted Aug. 27, 2009, 20 pages, published in PAIR.

Office communication in U.S. Appl. No. 12/024,490, mailed Jul. 22, 2009, 16 pages, published in PAIR.

Amendment After Final Rejection in U.S. Appl. No. 12/024,490, submitted Sep. 22, 2009, 28 pages, published in PAIR.

Office communication in U.S. Appl. No. 11/702,321, mailed Feb. 20, 2009, 19 pages, published in PAIR.

Amendment in U.S. Appl. No. 11/702,321, submitted May 8, 2009, 21 pages, published in PAIR.

Notice of Allowance and Fee(s) Due in U.S. Appl. No. 11/702,321 mailed Aug. 11, 2009, 20 pages, published in PAIR.

Office communication in U.S. Appl. No. 11/702,320, mailed Aug. 12, 2009, 9 pages, published in PAIR.

Office communication in U.S. Appl. No. 11/702,325, mailed Aug. 15, 2008, 14 pages, published in PAIR.

Amendment in U.S. Appl. No. 11/702,325, submitted Nov. 17, 2008, 38 pages, published in PAIR.

Office communication in U.S. Appl. No. 11/702,325, mailed Feb. 10, 2009, 8 pages, published in PAIR.

Response with Terminal Disclaimer in U.S. Appl. No. 11/702,325, submitted May 5, 2009, 5 pages, published in PAIR.

Office communication in U.S. Appl. No. 11/702,325, mailed Aug. 28, 2009, 13 pages, published in PAIR.

Office communication in U.S. Appl. No. 11/702,328, mailed May 27, 2009, 28 pages, published in PAIR.

Amendment in U.S. Appl. No. 11/702,328, submitted Aug. 14, 2009, 33 pages, published in PAIR.

Office communication in U.S. Appl. No. 11/702,328, mailed Sep. 11, 2009, 4 pages, published in PAIR.

Response to Interview Summary n U.S. Appl. No. 11/702,328, submitted Sep. 18, 2009, 6 pages, published in PAIR.

Notice of Allowance and Fee(s) Due in U.S. Appl. No. 12/024,490, mailed Nov. 2, 2009, 14 pages, published in PAIR.

Amendment in U.S. Appl. No. 11/702,325, submitted Nov. 2, 2009, 25 pages, published in PAIR.

Amendment in U.S. Appl. No. 11/702,320, submitted Nov. 3, 2009, 24 pages, published in PAIR.

Office communication in U.S. Appl. No. 11/702,328, mailed Oct. 5, 2009, 23 pages, published in PAIR.

Amendment After Final Rejection in U.S. Appl. No. 11/702,328, submitted Nov. 12, 2009, 22 pages, published in PAIR.

Response to Office Communication in U.S. Appl. No. 12/022,485, submitted Jan. 20, 2010, 7 pages, published in PAIR.

Office Communication in U.S. Appl. No. 12/025,394 mailed Jan. 22, 2010, 7 pages, published in PAIR.

Amendment under 37 C.F.R. Sec. 1.312 in U.S. Appl. No. 12/024,490, submitted Feb. 2, 2010, 85 pages, published in PAIR.

Amendment in U.S. Appl. No. 12/025,394, submitted Apr. 22, 2010, 17 pages, published in PAIR.

Amendment in U.S. Appl. No. 11/698,409, submitted May 17, 2010, 16 pages, published in PAIR.

* cited by examiner

FIG. 9
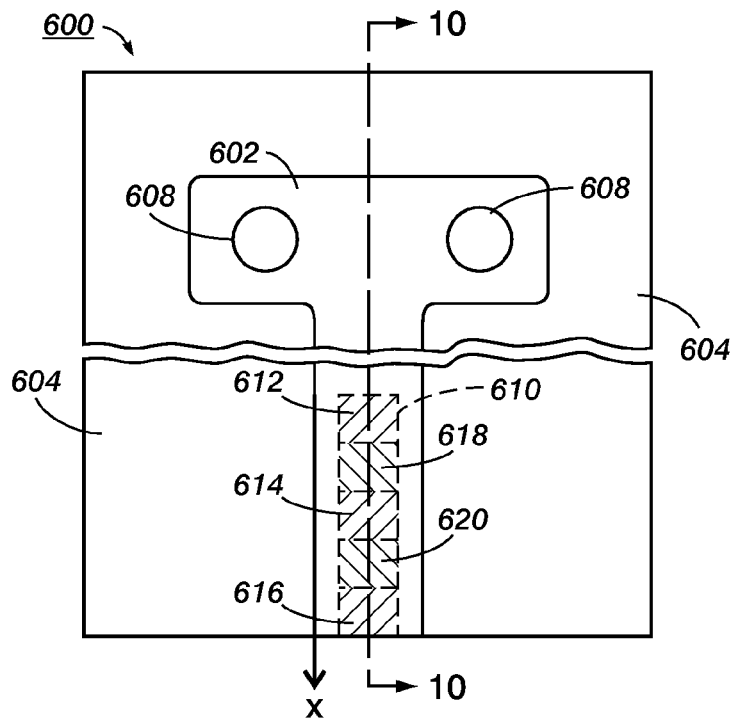
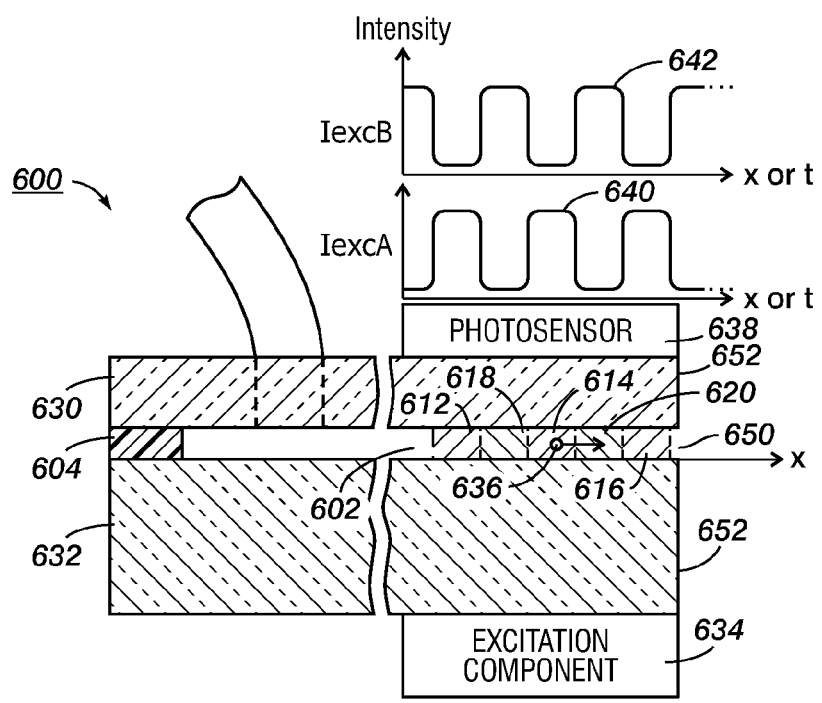
FIG. 10

US 7,763,856 B2

PRODUCING TIME VARIATION IN EMANATING LIGHT

The following applications, each of which is hereby incorporated by reference in its entirety, might be regarded as related to this application: "Sensing Photon Energies Emanating from Channels or Moving Objects", U.S. patent application Ser. No. 11/315,386, now published as U.S. patent Publication No. 2007/0146704; "Sensing Photon Energies of Optical Signals", U.S. patent application Ser. No. 11/315,926, now published as U.S. Patent Publication No. 2007/0147189; "Sensing Photons from Objects in Channels", U.S. patent application Ser. No. 11/315,992, now published as U.S. patent Publication No. 2007/0145249; "Obtaining Analyte Information", U.S. patent application Ser. No. 11/316,303, now published as U.S. patent Publication No. 2007/0148760; "Providing Light to Channels or Portions", U.S. patent application Ser. No. 11/316,660, now published as U.S. patent Publication No. 2007/0147728; "Method and System for Evaluation of Signals Received from Spatially Modulated Excitation and Emission to Accurately Determine Particle Positions and Distances", U.S. patent application Ser. No. 11/698,338; "Method and System Implementing Spatially Modulated Excitation or Emission for Particle Characterization with Enhanced Sensitivity", U.S. patent application Ser. No. 11/698,409; "Obtaining Information From Optical Cavity Output Light", U.S. patent application Ser. No. 11/702,249; "Photosensing Optical Cavity Output Light", U.S. patent application Ser. No. 11/702,250; "Distinguishing Objects", U.S. patent application Ser. No. 11/702,328; "Encoding Optical Cavity Output Light", U.S. patent application Ser. No. 11/702,363; "Moving Analytes and Photosensors", U.S. patent application Ser. No. 11/702,470; "Producing Sandwich Waveguides", U.S. patent application Ser. No. 11/777,661; "Producing Fluidic Waveguides", U.S. patent application Ser. No. 11/777,712; and "Obtaining Information from Time Variation of Sensing Results", U.S. patent application Ser. No. 12/022,485.

BACKGROUND OF THE INVENTION

The present invention relates generally to techniques that produce time variation in light emanating from objects. More specifically, techniques can use excitation arrangements to produce time variation in light emanating from objects that are moving relative to other components such as photosensors.

Various techniques have been proposed for using light emanating from objects. For example, U.S. Patent Application Publication No. 2007/0145249 describes a fluidic structure with a channel along which is a series of sensing components to obtain information about objects traveling within the channel, such as droplets or other objects carried by fluid. A sensing component includes a set of cells that photosense a range of photon energies that emanate from objects. A processor can receive information about objects from the sensing components and use it to obtain spectral information. Similar techniques are described, for example, in U.S. Patent Application Publication Nos. 2007/016704, 2007/0147189, and 2007/0147728.

Also, various flow cytometry techniques have been proposed.

It would be advantageous to have improved techniques for using light emanating from objects, including improved techniques for producing time variation in such light.

SUMMARY OF THE INVENTION

The invention provides various exemplary embodiments, including methods and apparatus. In general, the embodiments involve excitations between which are non-interference-like transitions.

These and other features and advantages of exemplary embodiments of the invention are described below with reference to the accompanying drawings.

BRIEF DESCRIPTION OF THE DRAWINGS

FIG. 9 is a top view of an article that can include an excitation arrangement and that can be included in an encoding component as in FIG. 2.

FIG. 10 is a cross-sectional view of an implementation of an article similar to that in FIG. 9, taken along the line 10-10, together with graphs of sensed intensities.

DETAILED DESCRIPTION

Figure 1:
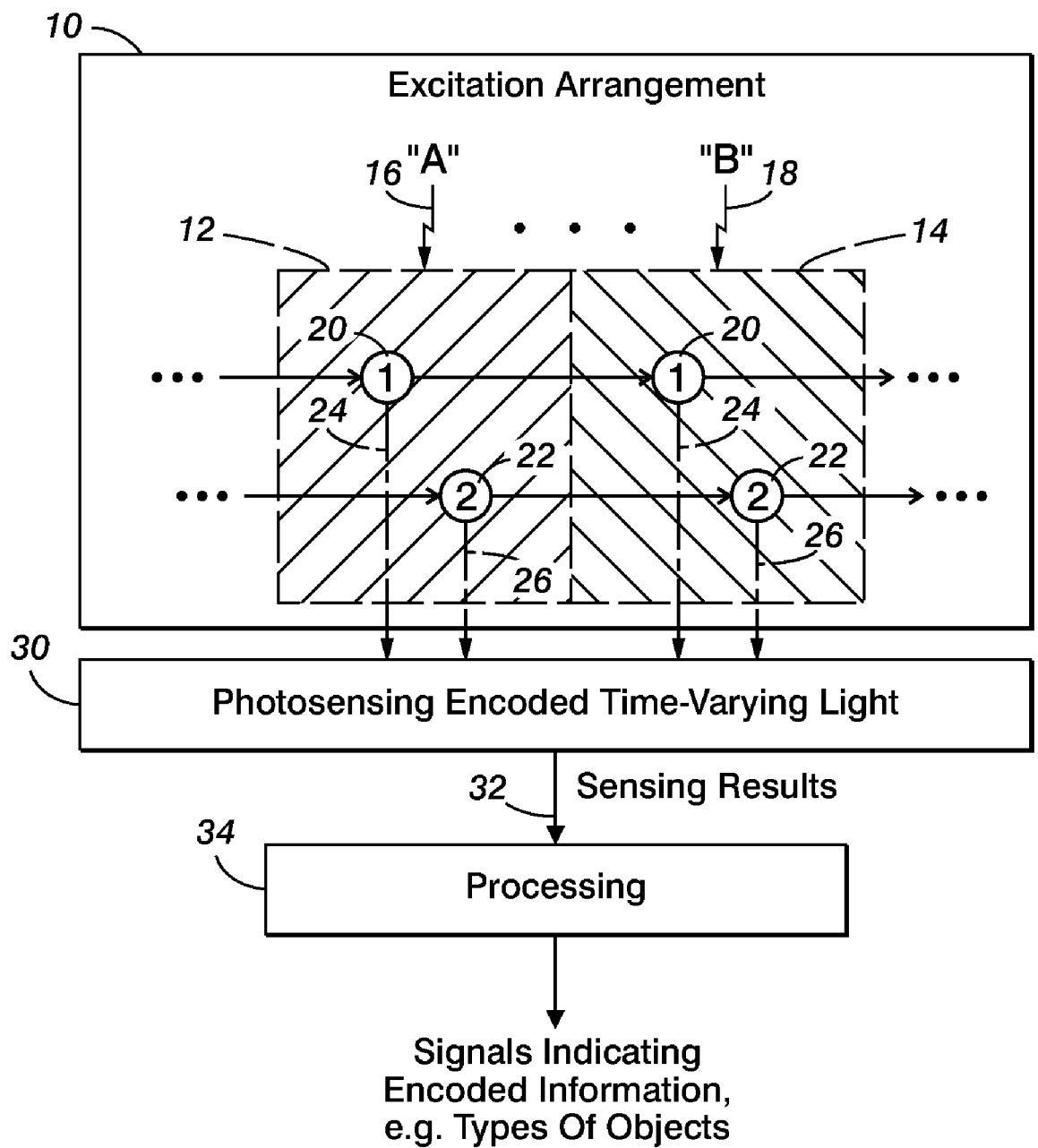
FIG. 1 is a schematic diagram showing features of techniques in which an excitation arrangement produces time variation in light emanating from an object.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information. A surface at which photosensing occurs is referred to herein as a "photosensitive surface".

The various exemplary implementations described below address problems that arise in obtaining information about a moving object such as a biological cell, a virus, a molecule, or a submolecular complex, such as in flow cytometry. Flow cytometry has become an indispensable tool in clinical diagnostics, such as in diagnosing cancer, AIDS, and infectious diseases during outbreaks, and also in microbiology and other areas. The cost and size of existing cytometers preclude their use in field clinics, water monitoring, agriculture/veterinary diagnostics, and rapidly deployable biothreat detection.

A number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement takes place in a fluidic channel in which cells traverse a detection region, typically at a speed of up to several meters per second. In the detection region, focused laser light (typically with an elliptical focus of 80 µm×40 µm) excites the dyes on the cells. The resulting fluorescent light can be collected by a microscope lens, sorted by band pass filters, and detected by PMTs or avalanche photodiodes (APDs). For each spot excitation, a respective set of filters and detectors is needed, which is costly and leads to bulky devices with strict requirements necessary to maintain optical alignment. Since the detection region is small and objects traverse it rapidly (typical dwell times are around 10 µsec), such flow cytometers have serious signal-to-noise (S/N) ratio issues for weakly fluorescing cells. These issues become more acute if multiple targets must be characterized and distinguished in some way, such as by counting.

A major cost in flow cytometry applied in clinical diagnostics is cost of reagents (e.g. antibodies and conjugated dyes). There are two ways to reduce the amount of consumables: First, one can reduce the required amount of analyte, e.g. by employing microfluidic techniques; and second, one can reduce the amount of consumable per analyte volume. Reducing amounts used would, however, reduce fluorescent intensity. It would be valuable to be able to overcome this constraint with a cost-effective and reliable technique to detect and distinguish weakly emitting cells.

Previous proposals to address these problems have involved spatially modulated single-color excitation to improve S/N ratios and to shift the detection limit toward weaker emitting cells. Spatial resolution can be maintained or improved in comparison with previous flow cytometry techniques, because fluorescing light is spatially modulated over a comparably large detection region; this is helpful because spatial resolution affects maximum detection or count rate of a device. But single-color techniques are limited, whether excitation is performed in a black/white approach or with a single-color interference pattern from a light source. Also, single-color techniques can encounter problems with wavelength sensitivity and bleaching of dyes. Because of low wavelength sensitivity, many flow cytometers with filter-PMT combinations are also constrained to use dyes with substantially different fluorescence wavelengths.

In addressing such problems, some exemplary implementations described below employ excitation sources in which different excitations have a non-interference-like transition between them. Some such techniques can be implemented with high spatial resolution without the limitations of single-color techniques. Such techniques can be implemented with multiple colors, including various visible range colors, or with intermediate intensities, such as gray levels; some such techniques might also be advantageously implemented even with single-color excitation. By using spatially interdigitated, patchwork-like, or otherwise patterned arrangements of multiple colors or gray levels, such techniques also alleviate the wavelength sensitivity and dye bleaching problems, so that objects such as cells can be characterized and distinguished based on responses to different excitation wavelengths. Use of multiple colors may be compatible with particle identification based on native fluorescence; in particular, spatial modulation with multiple colors might allow detection of differences in fluorescence spectra and intensities that result from differences in excitation/absorption spectra, and even the very small differences that occur in native fluorescence spectra might be detectable.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, laser diodes (LDs), light emitting diodes (LEDs), superluminescent LEDs (SLEDs), resonant cavity LEDs, sources of broadband light that is spectrally filtered such as with a monochromator, and so forth.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant CM less than c, then M has an index of refraction $n_M = c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon^* c$, where $\epsilon = 1/n_{EFF} \leq 1$ and $n_{EFF}$ is an effective index of refraction for the segment, optical distance $D(\epsilon) = d/\epsilon$. An optical distance may be referred to herein as an "optical thickness", such as where light is propagating through a thickness of material.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry".

In general, sensors, processors, and other such items may be included in a system in which they are operated automatically or partially automatically. As used herein, the term "system" refers to a combination of two or more parts or components that can perform an operation together. A system may be characterized by its operation; for example, an "object distinguishing system" is a system that operates somehow to distinguish objects.

Within a system, device, or other article, components and parts may be referred to in a similar manner. One component of an object distinguishing system, for example, can be described as an "encoding component", in some cases referred to as an "encoding arrangement", in either case meaning that the component or arrangement operates to encode information; similarly, a system can include an "excitation component", in some cases referred to as an "excitation arrangement", in either case meaning that the component or arrangement operates to provide excitation, such as illumination; various other components are described below. In addition, a component or part may be identified by characteristics other than its operation.

In FIG. 1, excitation arrangement 10 provides excitations 12 and 14, each of which can result from illumination, represented by arrows 16 and 18, labeled "A" and "B" respectively. A and B could, for example, identify two different photon energy distributions within an application's range of photon energies. Whether in the context of excitation or otherwise, a photon energy distribution is sometimes referred to herein as a "spectral distribution" or, more simply, a "spectrum". Spectral distributions that differ only in scale, so that one can be obtained from another simply by multiplying intensities at all energies by the same scaling factor, are sometimes described herein as having the same "spectral shape".

As used herein, the term "white", in a given implementation, refers to light with a spectrum that approximates maximum available intensities across the implementation's full range of photon energies (which could be broad band, a combination red, green, and blue, or another appropriate combination); the term "black" refers to the opposite of white, i.e. minimum available intensities across the full range, with the ideal being no light and therefore zero intensities. In excitation spectra, for example, light without maximal intensities across the full range as in white may be characterized as having a "gray level", such as one of the gray levels between white and black, or as having a "color", such as if it includes predominantly photon energies in a subrange, e.g. one of the colors in the visible range of wavelengths or in the infrared or ultraviolet ranges, or possibly a combination of such colors. For example, arrows 16 and 18 could represent excitation of colors or gray levels A and B, respectively, such as red and green, two different intensities with the same or different spectral shapes, or any other appropriate combination of different spectra in which each spectrum is neither white nor black, with the difference in colors or gray levels also being shown by the different hatching of excitations 12 and 14. Spectra that are neither black nor white are sometimes referred to herein as "non-binary spectra", and a non-binary spectrum of an excitation is sometimes referred to herein as a "non-binary excitation spectrum", while an excitation with a non-binary spectrum is sometimes referred to as a "non-binary excitation".

Objects 20 and 22 are moving objects traveling along respective paths. Objects 20 and 22 could, for example, be in a series of objects traveling through a fluidic channel or in an array of objects traveling in a scanning movement. The term "path" is used herein in the general sense of a series of positions and/or configurations that a moving and/or varying object can have during its motion and/or variation. For generality, a part of a path is sometimes referred to herein as a "segment", which could encompass any continuous series of one or more positions and/or configurations within a path.

In the illustrated example, each of objects 20 and 22 has a path that includes a sequence of segments that includes a preceding segment in which it receives excitation 12 from excitation arrangement 10 and a following segment in which it receives excitation 14. Since excitations 12 and 14 both have non-binary spectra and their spectra are different, each of objects 20 and 22 therefore receives a sequence of excitations that includes at least two different non-binary excitation spectra. Furthermore, as suggested by the boundary at which excitations 12 and 14 meet, a "non-interference-like transition" occurs between excitations 12 and 14. As used herein, a "non-interference-like transition" is a transition of a type that could not occur in a single, monochromatic interference pattern, and therefore cannot be produced merely by the interference pattern from a single laser or another monochromatic light source or another monochromatic interference pattern that approximates such an interference pattern even though produced in a different way; such interference patterns are sometimes referred to herein as "single interference patterns". It follows that all transitions to or from a binary excitation are non-interference-like transitions. Several other examples of non-interference-like transitions are describe below in relation to exemplary implementations; as will be seen, non-interference-like transitions can occur between many different combinations of non-binary excitations and, in general, can have any appropriate duration and other features, provided the definition set forth above is met. As illustrated below, excitation with non-interference-like transitions can produce a broad repertoire of time variations in emanating light, extending well beyond black/white or single interference pattern techniques, and the repertoire is made even broader with non-binary excitations such as gray levels or colors. Furthermore, time-varying excitation in response to trigger signals can also be used to broaden the repertoire, with or without non-interference-like transitions.

Object 20 emanates light represented by arrows 24 in response to excitations 12 and 14, while object 22 emanates light represented by arrows 26; in each case, light could emanate, for example, by emission, reflection or other scattering, and/or transmission. Due to the different spectra of non-binary excitations 12 and 14 and the non-interference-like transition between them, information is encoded in light emanating from objects 20 and 22 respectively; the encoding is not, however, limited by the constraints applicable to black/white or single interference pattern excitation, facilitating a wide range of information encoding possibilities that would be difficult with black/white or single interference pattern encoding. Several examples of information encoding with non-binary excitations having non-interference-like transitions between them are described below in relation to exemplary implementations.

In general, an application that employs excitation arrangement 10 will include constraints on excitations and on emanating light. For example, the emanating light resulting from excitations 12 and 14 must include light within an application's range of photon energies and range of intensities. A constraint to the application's range of photon energies can mean, for example, that techniques as in FIG. 1 can be successfully used in a given application, e.g. flow cytometry, bio-chip readout, any suitable kind of analyte detection, or scanning of documents or other arrays of objects, provided excitation is provided that results in emanating photon energies within an application's energy range, even though emanating light might also include photon energies that are outside the application's range and that might not interact with other components as light in the application's range. Similarly, a constraint to an application's range of intensities can mean that techniques as in FIG. 1 can be successfully used in a given application provided excitation is provided at intensity levels that result in emanating photon energies within an application's intensity range; in general, an excitation light intensity level that is between and distinguishable from the maximum and minimum levels of the application's intensity range for a given spectrum shape is sometimes referred to herein as an "intermediate intensity" or, in some contexts in which light has approximately uniform intensity across an application's range of photon energies, as a "gray level".

The term "object" is used herein in the general sense of any distinguishable thing about which information can be obtained by a sensor and included in its sensing results. In some implementations, sensors can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of signals other than emanating light.

Emanating light or other types of signals can "include information" in many ways, some of which are described below in relation to specific implementations. Various criteria could be used to determine whether emanating light or another type of signal includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or another type of signal satisfies an appropriate encoding criterion for specified information, the light or signal may be said to "encode" the information.

Similarly, sensing results, whether from photosensing emanating light or from another type of sensing, can "include information" in many ways, and similar encoding criteria could be applied as with signals. Where sensing results indicate one or more time-varying waveforms, the sensing results can be referred to as having "encoded time variation".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In a system in which sensing results, emanating light, or other signals can include information about characteristics of objects, an object "travels" or is caused "to travel" if the object has a succession of positions over time with respect to one or more parts or components of the system or one or more patterns or other features of the system's environment such that information about the object's traveling, e.g. about speed or other rate of displacement, can be included in the emanating light or other signals. An object that travels is sometimes also referred to herein as "moving" or as having "motion" or "movement", but an object's traveling may result from any appropriate motion of the object and/or motion of parts or components of the system or patterns or other features of its environment. In other words, motion of an object includes any relative movement between the object and parts or components of a system or patterns or features of the system's environment, such as an encoding or sensing component of the system or a pattern of excitation or of filtering or another environmental pattern or feature.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Emanating light that includes information about an object's traveling is sometimes referred to herein as "motion-affected" light, as including "motion-dependent information", or as having "motion-dependent encoding". For example, an object could travel by being conveyed in fluid, such as liquid, gas, or aerosol, along a path in which it receives excitation and, as a result, emanates motion-affected light; in such a case the object may be referred to as being "carried" by fluid. In another example, an object contained in or otherwise supported by a support structure could, while receiving excitation, travel due to relative scanning movement between the support structure and another component such as a photosensor, and it could emanate motion-affected light.

Although their paths could be similar as illustrated, each of objects 20 and 22 responds differently to excitations 12 and 14, so that its emanating light while receiving excitation 12 is different than its emanating light while receiving excitation 14. As a result of operation of excitation arrangement 10 in producing time variation in emanating light, each object's emanating light has information encoded in its time variation, such as time variations in intensity within an application's range of photon energies. Object 20, for example, could be an object of type "1" as shown, a type of object that responds to color or gray level A with high intensity emanating light, but to color or gray level B with low intensity; as a result, light emanating from object 20 would vary over time from high to low intensity. Conversely, object 22 could be an object of type "2" as shown, a type of object that responds in a complementary manner, responding to color or gray level A with low intensity emanating light and to color or gray level B with high intensity; as a result, light emanating from object 22 would vary over time from low to high intensity. Emanating light could vary in a variety of other ways, such as if excitations 12 and 14 have two different intensities of the same color, with a non-interference-like transition between them. The difference between time variation of emanating light from objects 20 and 22 would therefore encode information about their respective types.

The operation in box 30 photosenses a portion of the emanating light with information encoded in its time variation, represented by arrows 24 and 26, and provides photosensing results, represented by arrow 32. This operation can be implemented with any suitable photosensing component, some of which are described below. In general, sensing results from photosensing in box 30 take the form of analog or digital electrical signals, depending on the structure and circuitry included in the photosensing component. In whatever form, the sensing results can include at least part of the information that is encoded in the emanating light's time variation. Therefore, the processing operation in box 34 can use the sensing results from box 30 to obtain signals indicating some or all of the encoded information, such as the type of each object, and can therefore be referred to as a "decoding" operation. The results of decoding can be used in a wide variety of ways, some of which are described below in relation to specific implementations.

Information about an object, as obtained in FIG. 1, can be used for a wide variety of purposes. In exemplary implementations described below, such information can, for example, be used to distinguish objects. In some applications, such as where the distinguished objects are registration marks in documents or other images, appropriate subsequent operations can be controlled based on the results of distinguishing objects.

Excitation arrangement 10 in FIG. 1 could be implemented in many different ways, some of which are described below. In some exemplary implementations below, for example, an excitation component provides an excitation pattern that includes a longitudinal sequence of excitation regions of different non-binary colors or gray levels, between which are non-interference-like transitions. In others, an excitation component provides time-varying excitation in which non-interference-like transitions occur between intervals of non-binary excitation. As a result, emanating light from different regions or intervals will have different intensities, depending on the intensity of light emanating from an object in response to each region's color or gray level or each interval's excitation, so that time variation of the emanating light encodes information about the object's spectral interactions such as the spectra in which it and other similar objects absorb, fluoresce, or otherwise interact with light, i.e. about the type of the object.

Figure 2:
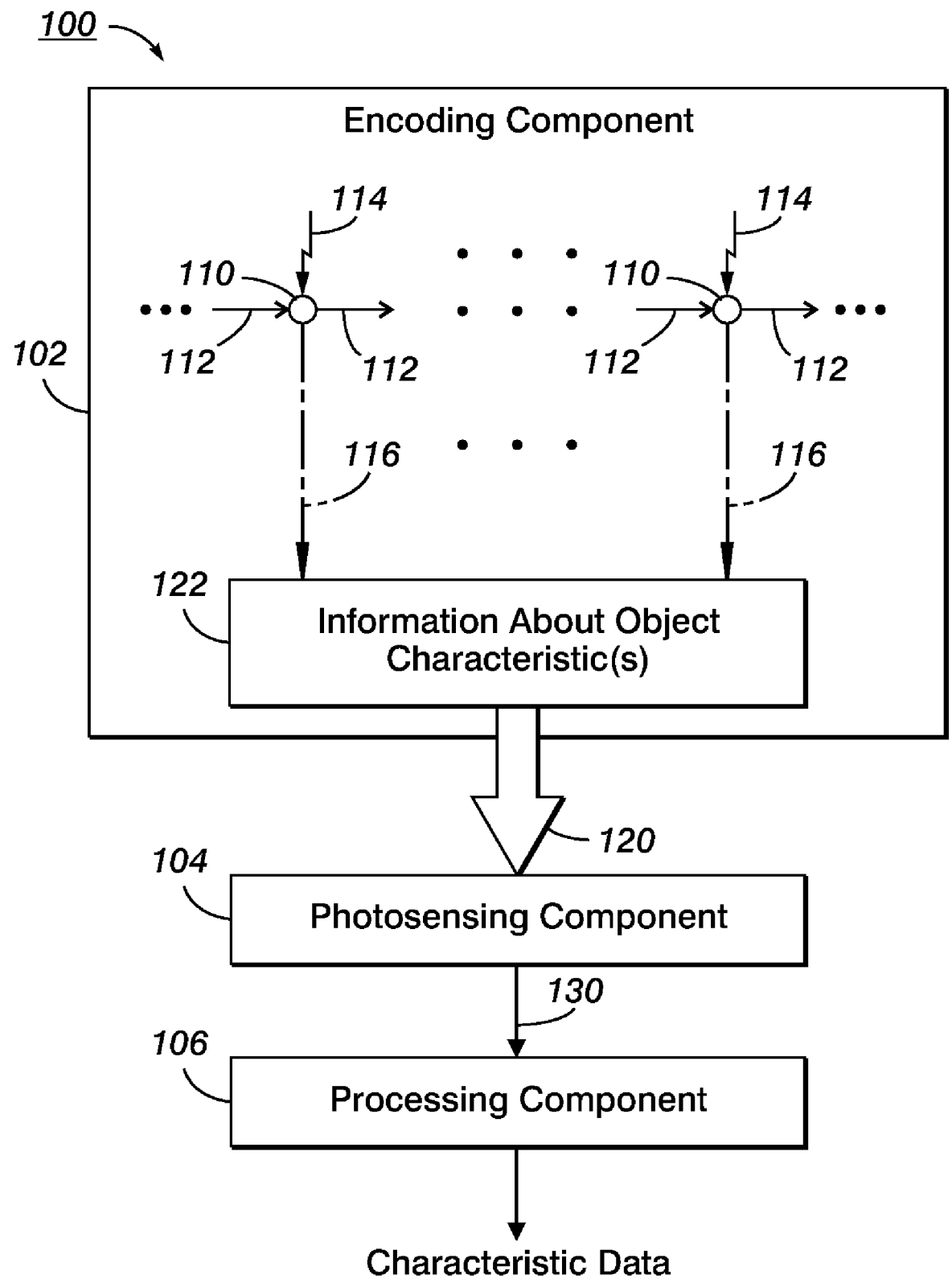
FIG. 2 is a schematic diagram showing components of a system in which light emanating from an object can include information about characteristics of the object.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding component 102 illustratively provides output light that includes information about one or more object characteristics. Photosensing component 104 responds to the output light, providing sensing results such as electrical output signals with information in a form that can be communicated to processing component 106, possibly after conversion to other forms, e.g. for storage, transmission, and processing, such as optical or other electromagnetic signal forms. Processing component 106 can use the sensing results from photosensing component 104 to obtain and/or provide characteristic data indicating information about one or more object characteristics.

Object 110 illustratively travels in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations.

Arrow 120 represents output light from encoding component 102. Box 122 between arrows 116 and arrow 120 illustrates that information about one or more characteristics of object 110 is included in the output light. As described below in relation to exemplary implementations, this information can be encoded in a variety of ways, including, for example, patterning excitation and/or patterning emanating light to obtain encoded output light represented by arrow 120.

Arrow 120 points to photosensing component 104, indicating that at least part of the encoded output light is illustratively sensed by component 104 to obtain sensing results. Based on the sensing results, component 104 provides electrical output signals represented by arrow 130. The electrical output signals can also include at least some of the information about object characteristics from box 120. As a result, processing component 106 can, in response to the electrical output signals, obtain and/or provide characteristic data indicating information about object characteristics.

Figure 3:
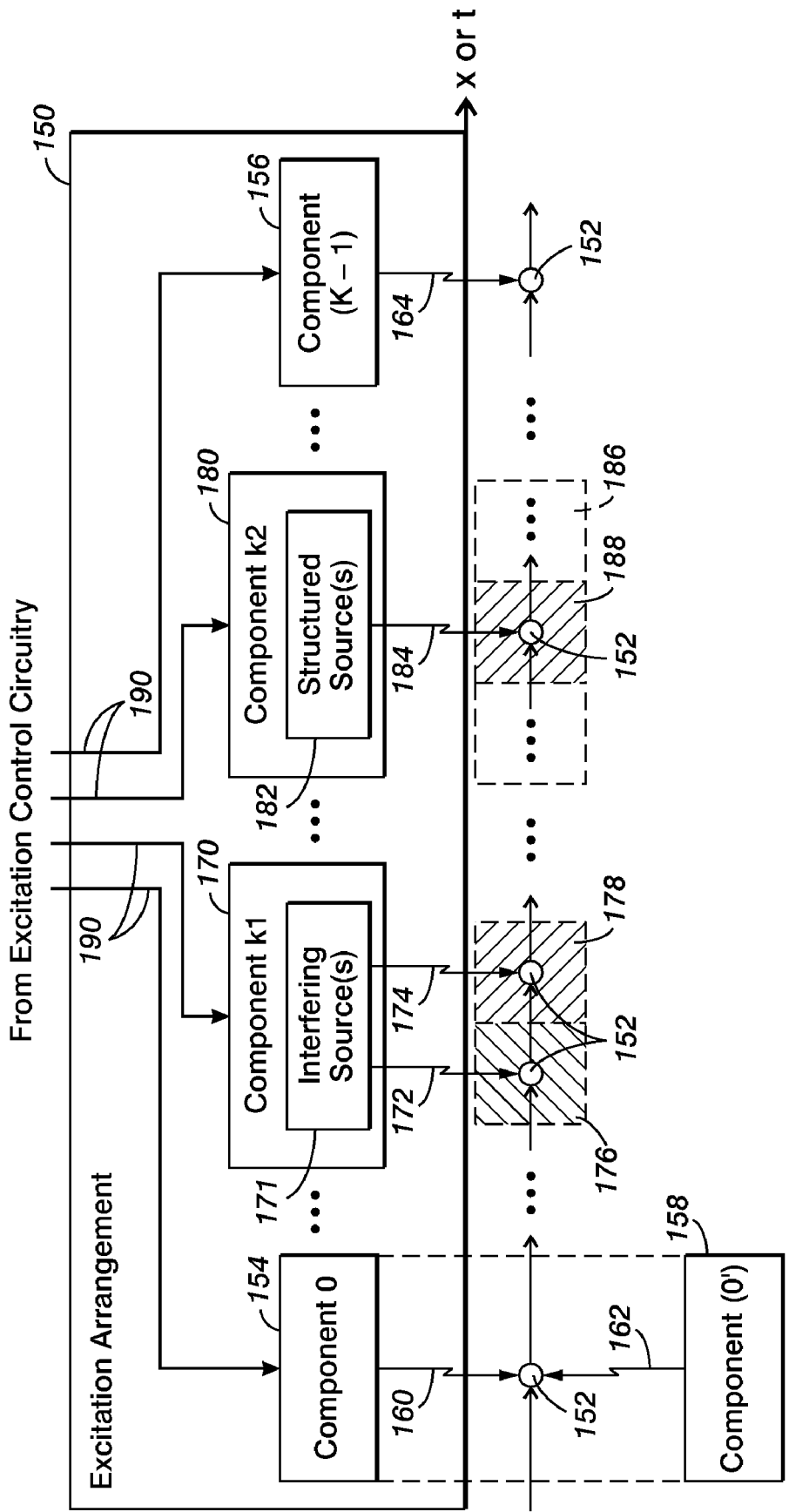
FIG. 3 is a schematic diagram of an excitation arrangement in an encoding component as in FIG. 2.
Figure 4:
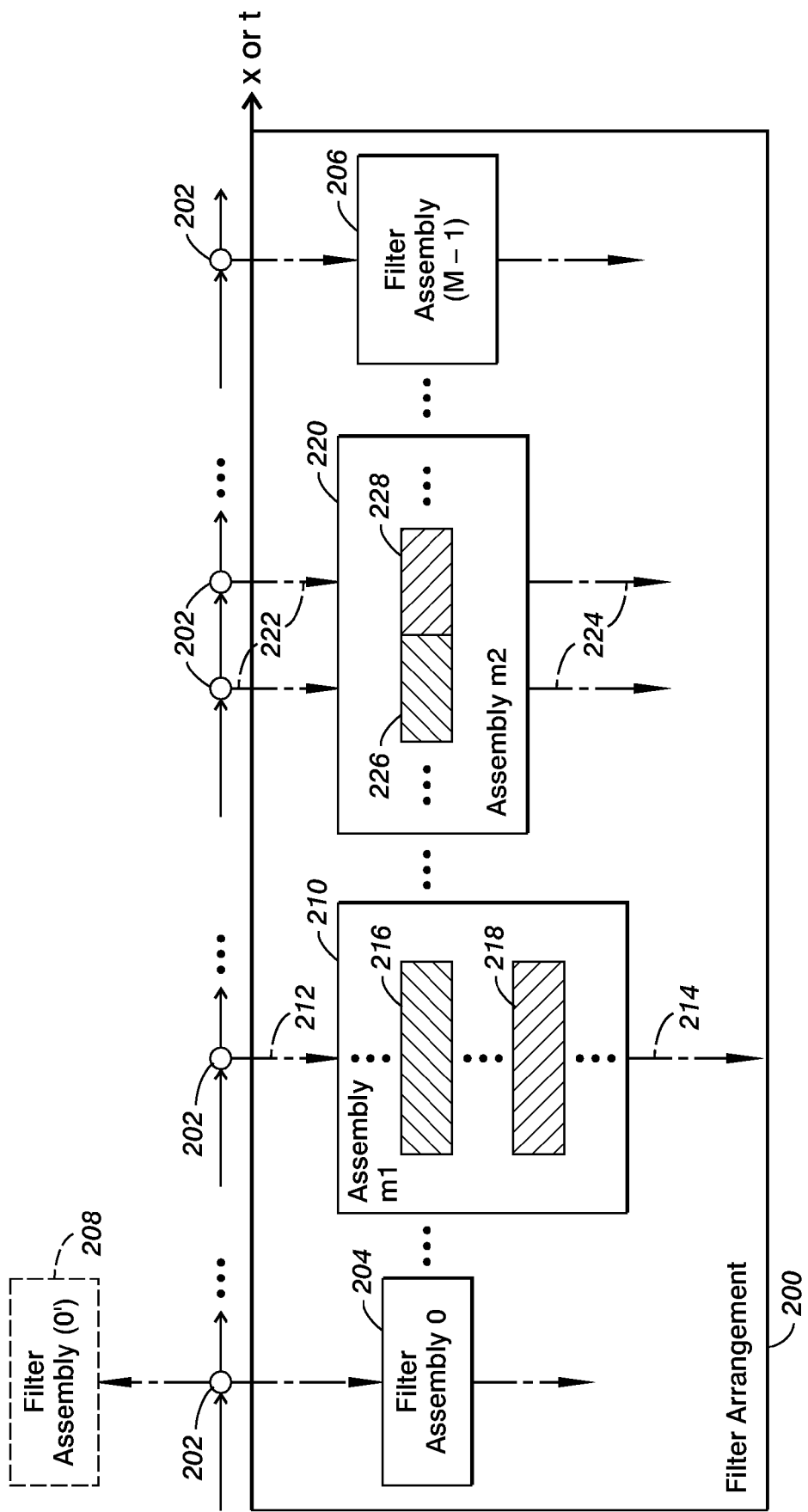
FIG. 4 is a schematic diagram of a filter arrangement in an encoding component as in FIG. 2.
Figure 5:
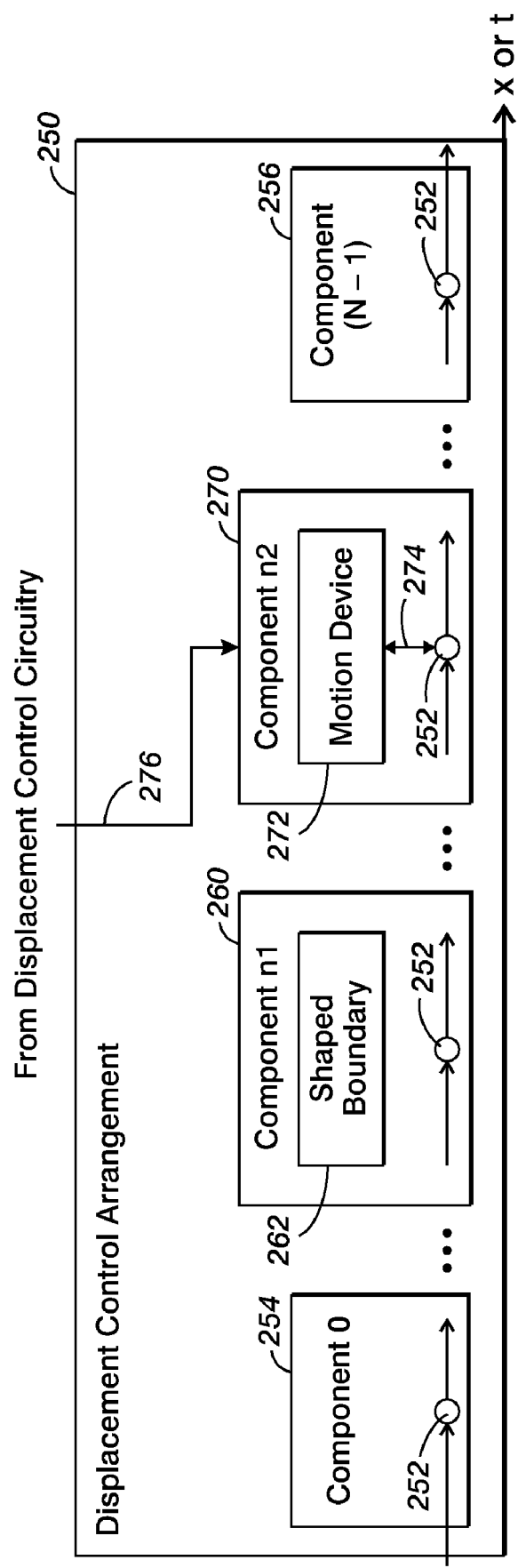
FIG. 5 is a schematic diagram of a displacement control arrangement in an encoding component as in FIG. 2.

Each of components 102, 104, and 106 in FIG. 2 could be implemented in a wide variety of different ways. FIGS. 3-5 illustrate several general features of implementations of encoding component 102, each of which involves an arrangement along a path traveled by a moving object.

In FIG. 3, excitation arrangement 150 is along a path traveled by moving object 152 as it emanates light within an encoding component such as component 102 in FIG. 2. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 152 may vary as it travels along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Patent Application Publication No. 2007/0145249, entitled "Sensing Photons from Objects in Channels", incorporated herein by reference in its entirety, or from other techniques, including obtaining information such as a trigger signal from an object's encoded signal.

The term "excitation component" refers herein to a part or component that provides excitation of any appropriate type, in response to which objects emanate light. For example, illumination of various kinds can cause objects to emanate light, so that many excitation components are light sources. Other types of excitation can also be provided, within the scope of the techniques described herein.

Excitation components can be combined and configured in many different ways, and all such combinations and configurations are encompassed herein by the general term "excitation arrangement". Some specific examples included herein employ interference in light from one or more light sources, and are therefore referred to as "interfering sources", while others involve structures that include one or more light sources and that provide a pattern of illumination, referred to herein as "structured sources". Within a given configuration of excitation components, relationships can be described in several ways. Of particular relevance is the pattern of illumination that can be produced, such as interfering sources or structured sources; such a pattern can include "excitation regions" and/or "excitation patterns"; the terms "excitation pattern" and "excitation region" are related, in that an excitation pattern includes one or more excitation regions, while an excitation region generally does not include other excitation regions within it. If a path travels through a "longitudinal sequence" of excitation regions, it passes through each of the regions on a respective segment of its path.

Several categories of longitudinal sequences of excitation region are described below in relation to exemplary implementations, including periodic patterns, chirp patterns, random patterns, and so forth, and various other categories could be identified. As used herein, the term "random" refers to a pattern that is non-periodic over the entire length of a longitudinal sequence of excitation regions; in contrast, a "periodic" sequence has at least one pattern that repeats more than once across the sequence's longitudinal length; and "chirp" sequences meet the above definition of random but can, with linearly varying time-scaling, meet the above definition of periodic, in effect being a sequence of periods of linearly changing frequency or wavelength. Any of these types of excitation sequences can be used to obtain "spatially modulated" emanating light, meaning emanating light that varies in time depending on position of an object from which it is emanating.

Although excitation components could be positioned in any appropriate way along a path, the exemplary implementations described below generally involve arrangements of one or more excitation components along the x OR t axis, and FIG. 3 shows several exemplary components within a sequence of K excitation components 154 through 156, with component 154 labeled "0" and component 156 labeled "(K−1)". Excitation components need not, however, be arranged on only one side of the path, but rather could be positioned at any suitable positions around the path, depending on how excitations from different components interact. Also, two or more excitation components could be at the same position or in overlapping position ranges along the x OR t axis, but displaced in a rotation direction; a configuration of excitation components that are sufficiently displaced in a rotation direction so that they are around the path is illustrated by component 158, representing a possible position of another excitation component labeled "(0')" in arrangement 150, on the opposite side of the path traveled by object 152 from component 154.

Arrow 160 schematically represents excitation from component 154, while arrow 162 represents excitation from component 158. Similarly, arrow 164 represents excitation from component 156. Although excitation from components 154 and 158 can be provided concurrently to object 152, as suggested by arrows 160 and 162, excitation from component 156, represented by arrow 164, is provided at a subsequent position and time of object 152.

Excitation component 170, labeled "k1", illustratively includes one or more interfering light sources 171, resulting in two or more different types of excitation, with two types represented by arrows 172 and 174. The excitation represented by arrow 172 occurs while object 152 travels along a segment of the path through region 176, while the type of excitation represented by arrow 174 occurs while object 152 travels along a subsequent segment of the path through region 178. Regions 176 and 178 therefore form a pattern in space, an example of "spatially patterned excitation" used herein to refer to excitation that occurs in a pattern in space, i.e. a "spatial pattern"; spatially patterned excitation could, for example, include multiple periods of a spatial pattern. In particular, the excitation in region 176 has a different photon energy spectrum than the excitation in region 178, so that regions 176 and 178 could be described as having "different colors" or "different gray levels" of excitation. Several specific examples in which spatially patterned excitation includes regions of different colors or different gray levels are described below in relation to exemplary implementations; as will be understood from some of the examples, the x-direction of a path as shown in FIG. 3 may not follow a straight line, so that regions 176 and 178 may not in fact be oriented along a straight line through components 154 through 156—in some implementations, regions 176 and 178 could each extend parallel to such a line and the path could go back and forth between regions 176 and 178.

Excitation component 180, labeled "k2", illustratively includes one or more structured light sources 182. In other words, light sources 182 are structured to provide spatially patterned excitation, represented by spatial pattern 186. In the illustrated example, arrow 184 represents excitation provided in region 188, one of a pattern of regions through which object 152 passes while receiving excitation from component 180. The complete pattern of regions is represented in FIG. 3 by pattern 186.

FIG. 3 also illustrates lines 190 through which each of components 154 through 156 can receive control signals from excitation control circuitry (not shown). For example, one or more of the components in excitation arrangement 150 could include trigger detecting circuitry (not shown) as described above, and the excitation control circuitry could, in response to the trigger detecting circuitry, provide control signals causing the component to provide excitation, either in a steady state or time-varying manner. As described below in relation to exemplary implementations, time-varying excitation can encode information in a way similar to spatially patterned excitation.

In FIG. 4, filter arrangement 200 is similarly along a path traveled by moving object 202 as it emanates light within an encoding component such as component 102 in FIG. 2. Filter arrangement 200 includes a combination of one or more filter assemblies along the path traveled by object 202.

The term "optical filter" or simply "filter" refers herein to a light-transmissive part or component that transmits light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit light within a subrange, sometimes referred to as a "band"; a band pass filter's type can therefore be specified by specifying the band or subrange of photon energies in which it transmits. A "blocking filter", which does not transmit any light in an application's range, can be viewed as a band pass filter with a band of zero bandwidth, while a "transparent filter", which transmits all light in an application's range, can be viewed as a band pass filter with a band that includes the entire range.

Filters can be combined and configured in many different ways, and all such combinations and configurations of one or more filters are encompassed herein by the general term "filter arrangement". A filter arrangement can include, for example, one or more "filter components", one or more "filter assemblies", and/or one or more "filter elements"; while the term "filter component" is generic, referring to any component that operates as a filter, the terms "filter assembly" and "filter element" are related and therefore a bit more specific, in that a filter assembly is a filter component that includes one or more filter elements, while a filter element is a filter component that generally does not include other filter elements within it. In general, filter elements and filter assemblies are sometimes also referred to as "masks".

Filter elements of various kinds could be included in filter assemblies, filter components, filter arrangements, and other combinations and configurations of filters, in a wide variety of ways. Within a given configuration of filters, relationships between filters can be described in a number of ways. For example, light can pass through a "sequence" of filters, meaning that specified light passes through the filters in a sequence: If a "radial sequence" of filters is along a path, for example, emanating light can pass through each of the filters in the sequence, beginning with the first and, after passing through each preceding filter, passing through the following filter; of course, light that is blocked by a preceding filter in a radial sequence would not reach its following filter. If a "longitudinal sequence" of filters is along a path, on the other hand, light emanating at each of a sequence of segments of the path passes through a respective filter in the longitudinal sequence.

Several other categories of filters are described below in relation to exemplary implementations, including shadow masks, periodic masks, chirp masks, random masks, and so forth, and various other categories could be identified. As used herein, the term "random" refers to a pattern that is non-periodic over the entire length of a longitudinal sequence of filters; in contrast, a "periodic" filter assembly has at least one pattern that repeats more than once across the assembly's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter assembly that, within a photon energy range of interest, transmits light of all energies, but with different parts of the filter transmitting the light at different intensities, such as black and white and/or different gray levels. Any of these types of filter assemblies can be used to obtain "spatially modulated" emanating light, meaning emanating light that varies in time depending on position of an object from which it is emanating.

Although filter assemblies could be positioned in any appropriate way along a path, the exemplary implementations described below generally involve arrangements of filter assemblies along the x OR t axis, and FIG. 4 shows several exemplary cross sections of filters within a sequence of M filter assemblies 204 through 206, with each cross section being taken parallel to the x OR t axis and with assembly 204 labeled "0" and assembly 206 labeled "(M−1)". Filter assemblies need not, however, be arranged on only one side of the path as shown, but rather could be positioned at any suitable positions around the path, depending on directional intensity variations of emanating light. Also, two or more filter assemblies could be at the same position or in overlapping position ranges along the x OR t axis, but displaced in a rotation direction; a configuration of filter assemblies that are sufficiently displaced in a rotation direction so that they are around the path is suggested by box dashed-line box 208 in FIG. 4, representing a possible position of another filter assembly labeled "(0')" in arrangement 200, on the opposite side of the path traveled by object 202 from filter assembly 204.

Filter assembly 210, labeled "m1", illustratively includes a radial sequence of filters through which light emanating from object 202, represented by arrow 212, can pass, with the output light from filter assembly 210 being represented by arrow 214. Filter assembly 210 could include any appropriate number of filters, with filters 216 and 218 being shown in FIG. 4.

The overall sequence of filter assemblies 204 through 206 illustrates a longitudinal sequence. Further, filter assembly 220 includes a longitudinal sequence of filters through which light emanating from object 202, represented by arrows 222, can pass, with the output light from filter assembly 220 being represented by arrows 224. Filter assembly 220 could include any appropriate number of filters in any appropriate longitudinal sequence, with adjacent filters 226 and 228 being shown in FIG. 4. Each of filters 226 and 228 could, for example, be a band pass filter, with the bands of filters 226 and 228 being sufficiently different to provide useful information about an emanation spectrum of object 202. Such a filter assembly is sometimes referred to herein as a "spatially patterned filter", because the filters it includes can be treated collectively as a single filter that has a pattern that varies as a function of position. Several examples of spatially patterned filters are described below in relation to exemplary implementations, and one or both of filters 216 and 218 in assembly 210 could also be implemented as a spatially patterned filter.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

Filter arrangements similar to those shown in FIG. 4 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a filter arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

In FIG. 5, displacement control arrangement 250 is similarly along a path traveled by moving object 252 as it emanates light within an encoding component such as component 102 in FIG. 2. Displacement control arrangement 250 includes a combination of one or more displacement control components, each of which is illustratively shown enclosing a respective segment of the path traveled by object 252. It would, of course, be possible to implement display control components in other ways, such as where an object travels along a path that is not enclosed within a channel or fluidic structure.

Although displacement control components could be positioned in any appropriate way along a path, the exemplary implementations described below generally involve arrangements of displacement control components along the x OR t axis, and FIG. 5 shows several exemplary components within a sequence of control components 254 through 256, with component 254 labeled "0" and component 256 labeled "(N−1)". Although each displacement control component in the sequence illustratively contains a respective segment of the path, it may be possible to implement displacement control components that affect displacement in overlapping segments of a path or that interact in other ways.

Control component 260, labeled "n1", illustratively includes shaped boundary 262, meaning that a boundary that extends partially or completely around the path, such as the boundary of a fluidic channel, has a shape that affects or controls displacement of object 252 as it travels along the path, such as by affecting its speed or other rate of displacement. Several examples of boundary shapes are described below in relation to exemplary implementations.

Control component 270, labeled "n2", illustratively includes motion device 272. Device 272 can illustratively cause lateral motion of a boundary in its segment of the path, as suggested by bidirectional arrows 274. Line 276 shows that device 272 can receive control signals from displacement control circuitry (not shown). Component 270 could also include trigger detecting circuitry (not shown), and the displacement control circuitry could respond to the trigger detecting circuitry by initiating operation of device 272, either in a steady state or time-varying manner. Examples of how device 272 could be implemented are described below in relation to specific implementations.

Figure 6:
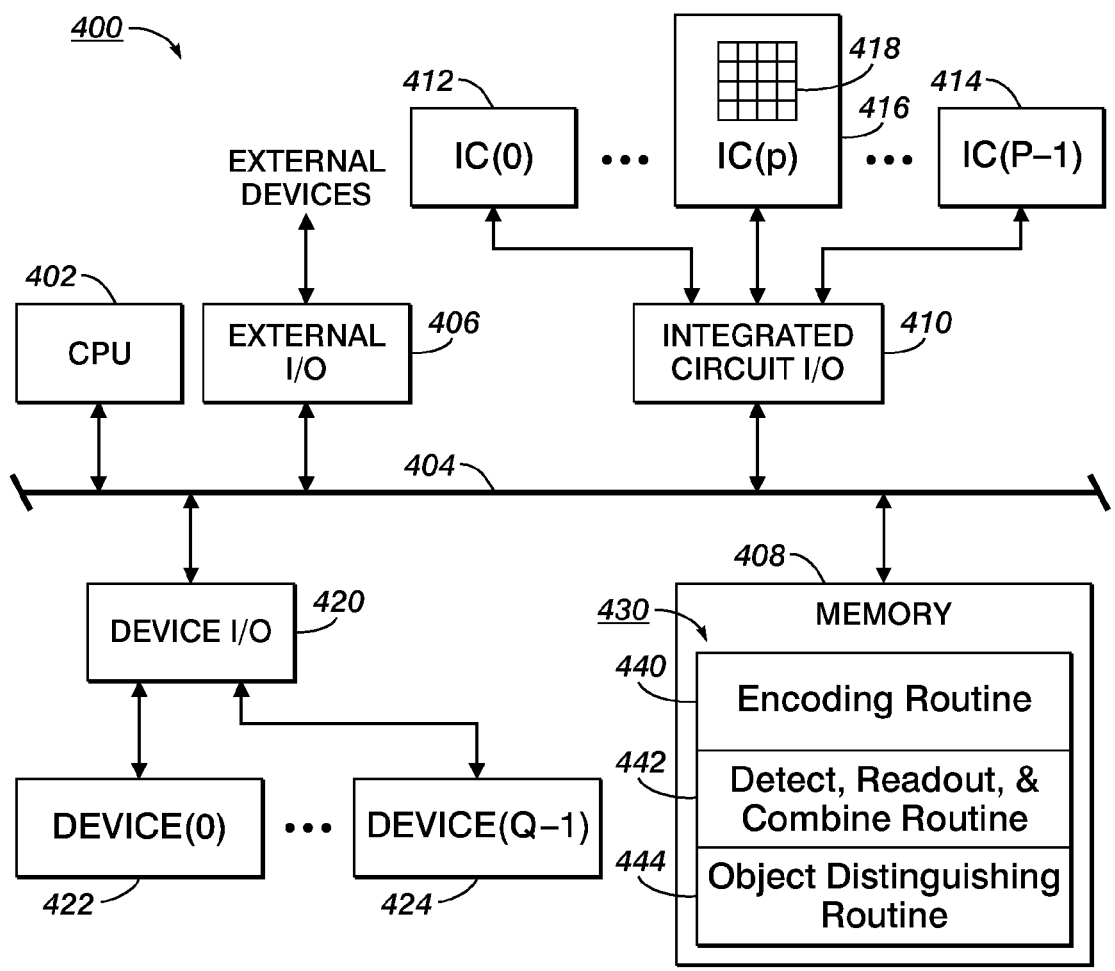
FIG. 6 is a schematic block diagram of a system in which components as in FIG. 2 can be implemented.

FIG. 6 illustrates system 400, an exemplary system that could implement components as in system 100 in FIG. 2. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as photosensing ICs; M ICs are illustrated in FIG. 6 by a series extending from IC(0) 412 to IC (P−1) 414. ICs 412 through 414 illustratively include IC(p) 416 with a photosensor array 418, which includes photosensing cells. Similarly, device I/O 420 is a component permitting CPU 402 to communicate with various devices in system 400, such as sensing and control devices; Q devices in system 400 are represented in FIG. 6 by device (0) 422 through device (Q−1) 424. In addition to excitation components as described above in relation to FIG. 3 and displacement control components as described above in relation to FIG. 5, devices 422 through 424 can include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include encoding routine 440; detect, readout, and combine routine 442; and object distinguishing routine 444. In addition, program memory 430 can also store a number of subroutines (not shown) that CPU 402 can call in executing routines 440, 442, and 444.

CPU 402 executes encoding routine 440 to encode information in light emanating from a moving object as it travels a path, i.e. information about characteristics of the object. In doing so, routine 440 can provide receive input signals from and provide output signals to devices 422 through 424. For example, to obtain appropriate motion of the object, CPU 402 can receive signals from sensors, perform computations to determine what fluidic operations are necessary, and then provide signals to activate pumps, metering electrodes, gates, and valves to produce appropriate relative movement between an object and other components of system 400 along its path. CPU 402 can also receive signals from trigger detecting devices and perform computations to determine what control signals to provide to excitation components, motion devices, or other components or devices in order to perform appropriate encoding in emanating light. Several examples of techniques that can be performed by encoding routine 400 are described below in relation to exemplary implementations.

In executing routine 442, CPU 402 can, for example, perform pre-sensing readout, obtain object information and sensing periods, perform sensing readout with sensing periods and analog adjustment, digitally adjust sensing results and store quantities for an object, and combine the quantities for an object to produce its characteristic data. Routine 442 could, for example, call a subroutine implemented as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid interference. Also, such a subroutine can follow a general strategy of performing a series of readout operations, after which information for an object is combined and its characteristic data is provided, although it would also be possible to provide the information from each readout operation immediately.

Figure 7:
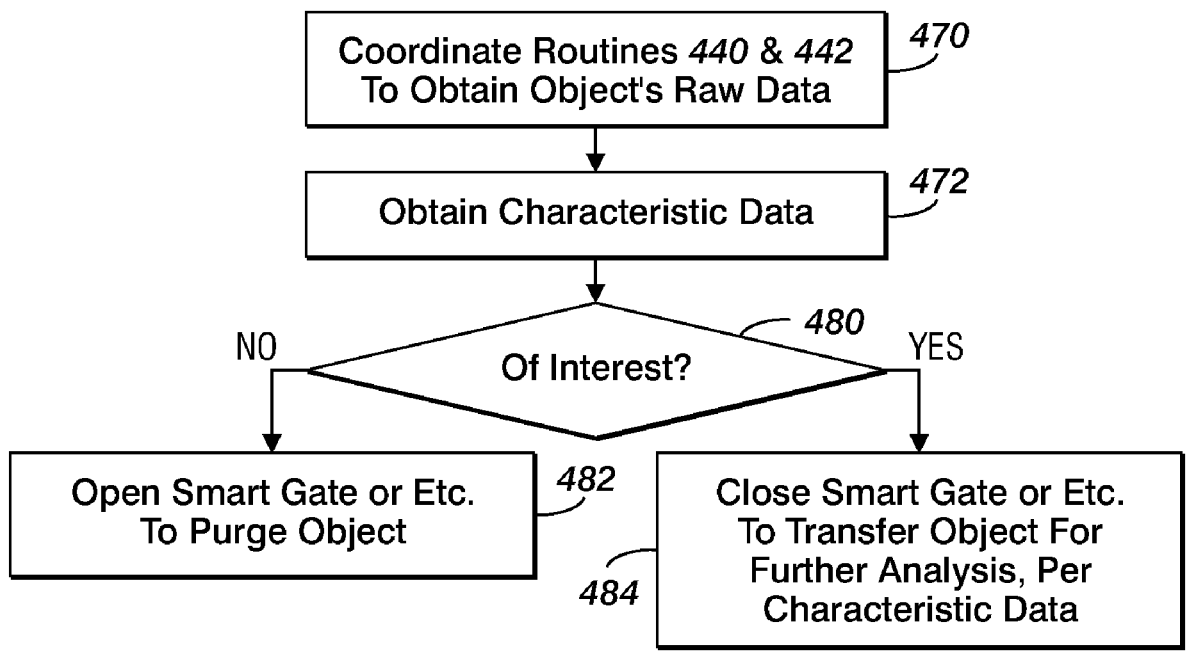
FIG. 7 is a flow chart showing general operations in an implementation of an object distinguishing routine as in FIG. 6.

FIG. 7 illustrates an example of how object distinguishing routine 444 in FIG. 6 could be implemented, using each object's raw data from routine 442 before it is used to obtain characteristic data for the object. Routine 444 can begin with the operation in box 470, which coordinates routines 440 and 442 as described above, obtaining an object's raw data, such as a data structure with photosensed quantities obtained from ICs 412 through 414.

The operation in box 472 receives the raw data from box 470, such as in the form of a handle or other item of data necessary to access a data structure. The operation in box 472 then uses the raw data to obtain the object's characteristic data, such as in one of the ways described below in relation to exemplary implementations. For example, an appropriate comparison technique could be used to obtain a comparison result indicating an object's type or other characteristic. The characteristic data from box 472 can indicate whether the object is of interest for further analysis, such as because it may be suspicious or harmful or, on the other hand, because it may be of interest for more refined analysis.

The operation in box 480 branches based on whether the object is of interest. If not, the operation in box 482 opens a smart gate or provides appropriate control signals to perform another operation to purge the object from the system. But if the object is of interest, the operation in box 484 ensures that the smart gate is closed or provides control signals for other suitable operations to transfer the object downstream so that a more refined or detailed analysis or other further analysis can be performed, possibly after concentration of the object with other similar objects by appropriate fluidic devices.

Figure 8:
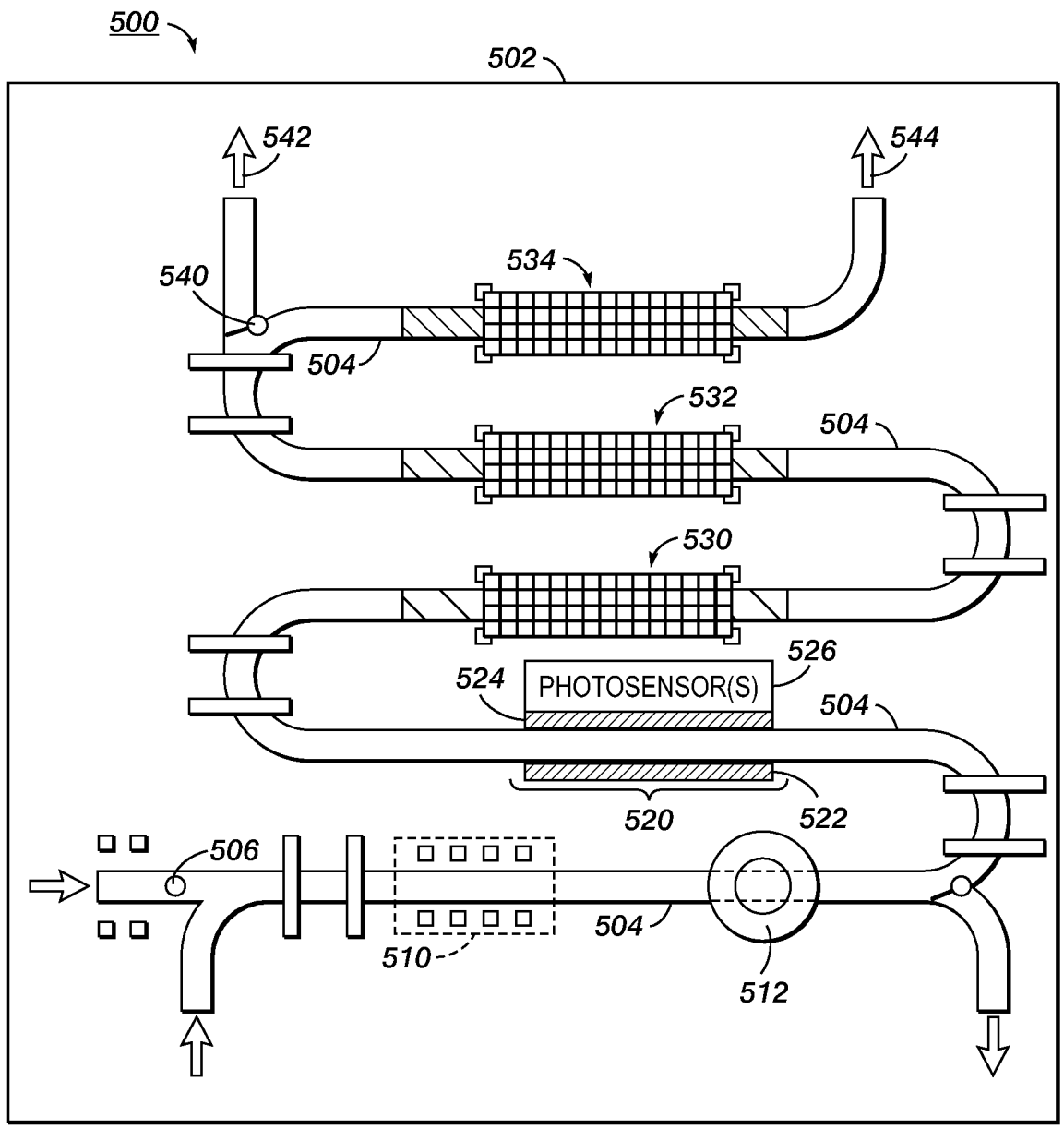
FIG. 8 is a schematic diagram of an analyzer in a fluidic structure, where the analyzer includes a system that can be implemented as in FIGS. 6 and 7.

FIG. 8 illustrates an application of a system as in FIGS. 6 and 7 in analyzer 500 on support structure 502, a fluidic structure. Defined in support structure 502 is serpentine channel 504 through which object 506 can travel, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can travel through a series of sensing components, each of which can obtain information about object 506.

The first two sensing components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics.

The next sensing component along channel 504 is emanating light encoder/photosensor 520, shown schematically in a cross-sectional view along an axis similar to the x OR t axis in FIGS. 3-5, although it would typically be implemented instead with components above and below channel 504, similarly to other sensing components described below. The schematic illustration of encoder/photosensor 520 includes excitation/displacement component 522, filter component 524, and photosensing component 526, all of which might be implemented in a variety of ways, including some of those described above and below.

After passing through encoder/photosensor 520, object 506 could be characterized without obtaining further information, or, as in the illustrated implementation, object 506 can continue through subsequent sensing components, illustratively including components 530, 532, and 534. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 8 is merely illustrative of a wide variety of implementations of the techniques described herein. For example, any appropriate fluidic or nonfluidic techniques could be used with a wide variety of different types of objects and various types of relative motion to gather various types of information about object characteristics.

FIG. 9 illustrates an example of article 600 with components that could be operated similarly to encoder/photosensor 520 in FIG. 8. Some features of article 600 can be understood from description in co-pending U.S. patent application Ser. No. 11/777,712, entitled "Producing Fluidic Waveguides", incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects; in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

As described below, article 600 can include two light-transmissive components, and FIG. 9 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 8. Ports 608 are openings through one of the light-transmissive components, allowing entry and exit of fluid into and out of channel portion 602.

FIG. 9 also shows excitation pattern 610 in dashed outline. Excitation pattern 610 illustratively includes a periodic two-color pattern, with regions 612, 614, and 616 having approximately the same photon energy spectrum in a range of possible excitation energies and with regions 618 and 620 also having approximately the same photon energy spectrum in the range, but different from that of regions 612, 614, and 616, as indicated by the cross-hatching. Between the regions are non-interference-like transitions, because the differences between the regions could not occur in a single interference pattern. Each of the regions has approximately the same length in the x-direction in FIG. 9, so that each of the excitation regions 612 through 620 can be characterized by its photon energy spectrum of excitation.

The cross section in FIG. 10 shows how light-transmissive components 630 and 632 are separated by material in non-channel portion 604. For example, component 630 and 632 can each include quartz or another suitable material such as glass or acrylic with an appropriate thickness such as approximately 0.3 mm or less; depending on the application, on stability of materials used, and size of objects being characterized, suitable thicknesses might range from a few millimeters down to 0.1 mm or even less. The optimum distance between them is determined primarily by the size of objects being characterized. For biological cells with typical dimensions of 10 µm, for example, the distance can be approximately 20 to 50 µm, maintained by material in non-channel portion 604, which could, for example, be a suitable photo-resist material such as SU-8 or another polymer material, photolithographically patterned to form the shape around channel portion 602. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, with exemplary dimensions for waveguiding being described in co-pending U.S. patent application Ser. No. 11/777,712, entitled "Producing Fluidic Waveguides", incorporated herein by reference in its entirety.

FIG. 10 also shows excitation component 634, illustratively on the lower surface of component 632 and operating to produce excitation pattern 610 within channel portion 602. Excitation component 634 could be in any other suitable position, e.g. component 630 could itself be implemented to be or to include an excitation component. As object 636 travels along a path through channel portion 602, light illustratively emanates from it in response to excitation pattern 610. A portion of the emanating light propagates through component 630, reaching photosensor 638; photosensor 638 is illustratively shown on the upper surface of component 630, but could be in any other suitable position, including supported on spacers above the upper surface of component 630 or, component 630 could itself be implemented to be or include a photosensor with a photosensitive surface facing channel portion 602. Photosensor 638 could, for example, be a single, large area photosensor (such as a photo-diode, an avalanche photo-diode (APD), or a photo-multiplier tube (PMT)), or an appropriate array of photosensing cells whose sensed intensities or other quantities could be combined to obtain a single photosensed intensity or other quantity.

The emanating light varies over time as object 636 travels through excitation pattern 610, depending on characteristics of object 636, such as its fluorescence, absorption, or scattering spectrum. The upper part of FIG. 10 includes two graphs illustrating intensity detected by photosensor 638 as two possible types of object 636 that emanate in response to different colors or gray levels, referred to as "A" and "B". Curve 640 in the lower graph illustrates the intensity as an object responsive to color or gray level "A" travels along the path, responding strongly to the photon energy spectra in excitation regions 612, 614, and 616, but responding weakly if at all to the photon energy spectra in excitation regions 618 and 620. Similarly, curve 642 in the upper graph illustrates the intensity as an object responsive to color or gray level "B" travels along the path responding strongly to the photon energy spectra in excitation regions 618 and 620 but responding weakly if at all to the photon energy spectra in excitation regions 612, 614, and 616.

As can be seen, the shapes of curves 640 and 642 are approximately complementary, except at the far left before the path reaches excitation pattern 610, where neither object is emanating light. The maximum intensities of emanation in response to excitations A and B are illustratively labeled as IexcA and IexcB, respectively, and are illustratively approximately equal, but could be different in magnitude. In a simple implementation, excitation regions 612, 614, and 616 could be red colored, having spectra with photon energies predominantly in the red wavelengths, while excitation regions 618 and 620 could be green colored, having spectra with photon energies predominantly in the green excitation wavelengths, and the two types of objects could respond respectively to red and green wavelengths. As suggested, curves 640 and 642 could be plotted based on the x-direction position of object 636, or based on the t-position within the time-varying output signal from photosensor 638, which could be provided continuously or by any suitable form of sampling, such as by periodic readout at an appropriate frequency.

As can be seen from curves 640 and 642, the output signal from photosensor 638 can be used to distinguish types of objects, and computational techniques for doing so are described below in relation to exemplary implementations. Appropriate computational techniques may be used that depend on features of excitation pattern 610. As described above, pattern 610 is "periodic", meaning that it has at least one pattern that repeats more than once across its longitudinal length. As a result, the curves 640 and 642 may differ only in phase, possibly resulting in ambiguity, a disadvantage that can arise in certain applications.

Where appropriate, this ambiguity can be avoided by choosing a duty cycle of the periodic pattern substantially different from 0.5 (e.g. 0.1 or 0.9) or even more efficiently with non-periodic patterns, some examples of which are described below in relation to exemplary implementations. Although there are many possible types of non-periodic patterns, certain types can both be relatively simple and also sufficient to provide useful additional information. As used herein, the term "random" refers to a pattern that is non-periodic over its entire length in a longitudinal direction; also, "chirp" patterns meet the above definition of random but can, with linearly varying time scaling, meet the above definition of periodic, in effect being a sequence of periods of linearly changing frequency or wavelength. Any of these types of excitation patterns or combinations of them can be used to obtain "spatially modulated" emanating light, meaning that the emanating light varies in time depending on position of an object from which it is emanating.

In the illustrated implementation, the end of channel portion 602 at right in FIG. 10 is open, providing an additional port 650 through which fluid can enter into or exit out of channel portion 602. Alternatively, article 600, instead of ending at transverse end surface 652, could extend to another area with ports similar to ports 608, such as with a part symmetrical about the position of surface 652; in this case, fluid could flow through channel portion 602 between ports 608 and similar ports at the opposite end of channel portion 602.

Figure 11:
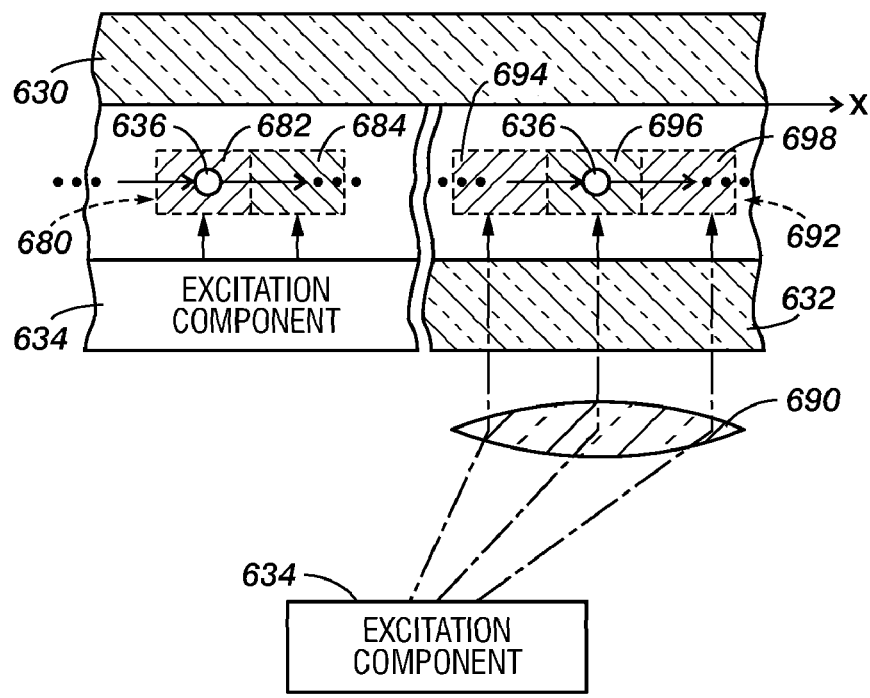
FIG. 11 is a partially schematic cross-sectional view showing two ways in which an excitation arrangement can be configured in an encoding component as in FIG. 2.

FIG. 11 illustrates two alternative implementations similar to FIG. 10, and with the same reference numerals, but with excitation component 634 differently positioned to illuminate channel portion 602 from the same direction as in FIG. 10. In each case, excitation component 634 could be implemented in any appropriate way, such as one of the ways described herein.

In the implementation at left, excitation component 634 also operates as one side of channel portion 602, replacing light-transmissive component 630 along at least a portion of the channel. An implementation like this would require that excitation component 634 have a structure that would not be damaged by exposure to materials in channel 602 and also that would confine fluid or other contents of channel 602 as necessary for operation. Excitation component 634 operates to provide excitation pattern 680, which illustratively includes excitation regions 682 and 684 of different colors or gray levels between which is a non-interference-like transition, but which could include any suitable number of regions having any appropriate colors and/or gray levels in any appropriate arrangement.

In the implementation at right in FIG. 11, excitation component 634 is sufficiently spaced apart from the lower surface of component 632 and provides excitation light that is imaged onto channel portion 602 by optical component 690, illustratively shown as a single lens, but which could be any suitable lens, lens system, microlens or selfoc array, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. The imaged excitation light produces excitation pattern 692 in channel portion 602, with excitation regions 694, 696, and 698. Regions 694 and 698 are illustratively of one color or gray level, while region 696 has another color or gray level, and there is a non-interference-like transition between them, but pattern 692 could be implemented with any appropriate number of regions having any appropriate combination of colors and/or gray levels in any appropriate arrangement.

Figure 12:
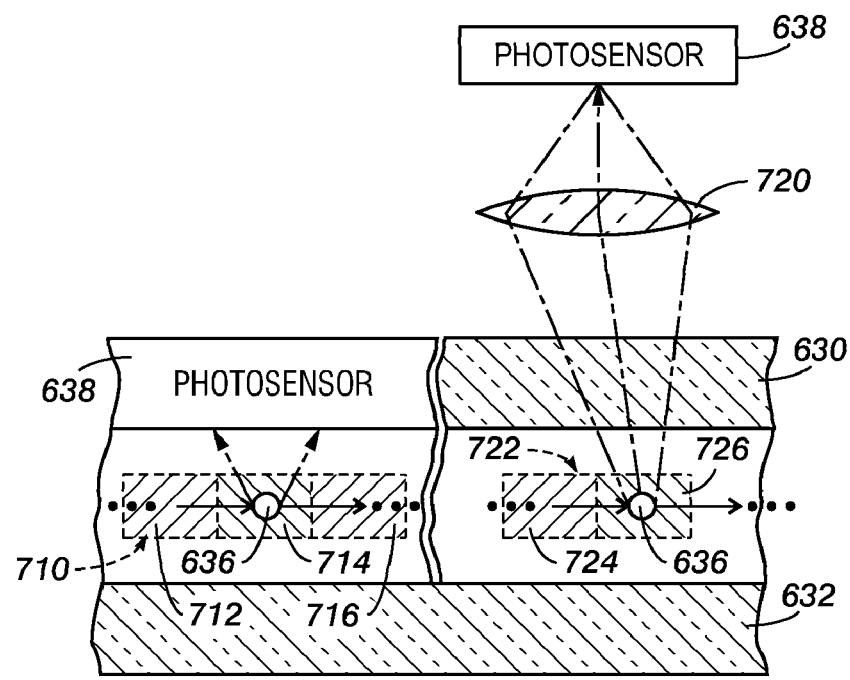
FIG. 12 is a partially schematic cross-sectional view showing two ways in which a photosensor can be configured in relation to an excitation arrangement in an encoding component as in FIG. 2.

FIG. 12 also illustrates two alternative implementations similar to that in FIG. 10, and with the same reference numerals, but with photosensor 638 in two alternative positions different than that in FIG. 10. In each implementation, photosensor 638 could be implemented in any appropriate way, such as one of the ways described herein.

In the implementation at left, photosensor 638 also operates as one side of channel portion 602, replacing light-transmissive component 630 along at least a portion of the channel. In this implementation, photosensor 638 must similarly be structured so that its photosensitive surface is not damaged or prevented from operating properly by materials in channel 602 and also so that it provides an appropriate boundary for fluids or other contents of channel 602. In the illustrated example, object 636 is passing through excitation pattern 710, which includes excitation regions 712, 714, and 716, with regions 712 and 716 having one color or gray level and region 714 having another and with non-interference-like transitions between adjacent regions; as in FIG. 11, however, any appropriate number of regions, any appropriate combination of colors and/or gray levels, and any appropriate arrangement of regions could be used.

In the implementation at right in FIG. 12, photosensor 638 is spaced away from the upper surface of component 630, and the emission cone from object 636 is imaged onto a photo-sensitive surface of photosensor 738 by optical component 720, illustratively shown as a single lens, but which could be any suitable lens, lens system, microlens or selfoc array, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Photosensor 638 illustratively receives light emanating from object 636 as it passes through excitation pattern 722, which includes regions 724 and 726 of different colors or gray levels between which is a non-interference-like transition; as above, pattern 722 could include any appropriate number of regions, any appropriate combination of colors and/or gray levels, and any appropriate arrangement of regions.

Figure 13:
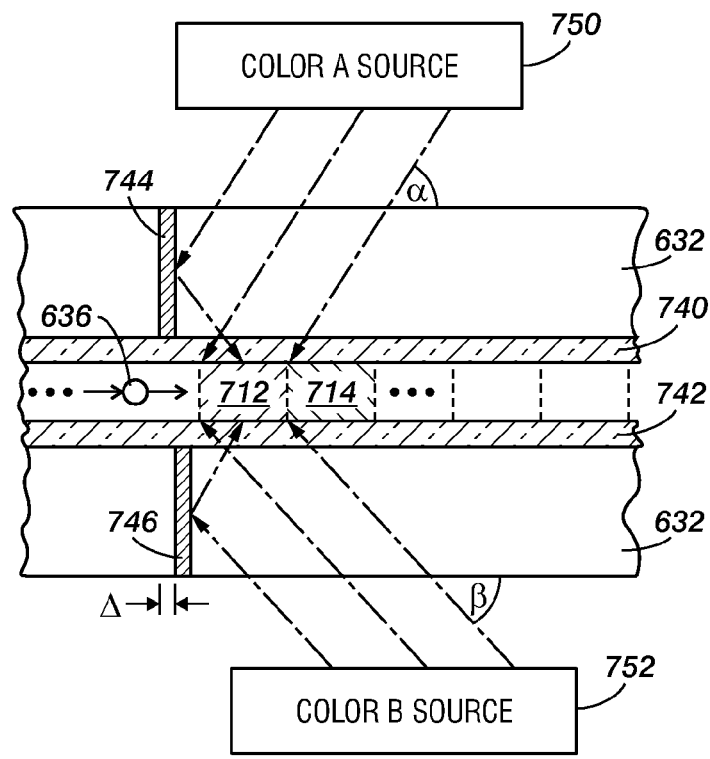
FIG. 13 is a partially schematic cross-sectional view showing an excitation arrangement that can be included in an encoding component as in FIG. 2.

FIG. 13 illustrates a cross section of a channel bounded by wall-like parts, similar to channel 504 in FIG. 8, and with reference numerals as in FIGS. 9-12 for similar items. The implementation in FIG. 13 could be included in a fluidic analyzer system as in FIG. 8 or in another appropriate system that can be used to obtain information about objects. For example, object 636 could be a biological cell, and the channel between wall-like parts 740 and 742 in FIG. 13 could receive object 636 in a fast flowing stream of fluid that surrounds object 636 and maintains laminar flow, providing ample flow at the center of the channel.

Excitation pattern 710 with regions 712 and 714 is produced in the implementation of FIG. 13 by superimposing two interference patterns in collimated narrow band light from two offset sources, such as lasers. The light from the sources is reflected into channel 602 by mirrors 744 and 746, which could be air gaps, metal layers, distributed Bragg mirror structures, or any other appropriate light reflective structures. Light from source 750 illustratively has a photon energy spectrum described as color "A", and is reflected by mirror 744 after entering at angle α, while light from source 752, with a photon energy spectrum described as color "B", is reflected by mirror 746 after entering at angle β. Mirrors 744 and 746 are offset slightly in the longitudinal direction, with the offset being illustrated in FIG. 13 as the distance Δ. Because of the difference in wavelength and the slight offset, sources 750 and 752 produce a combined interference pattern including regions 712, 714, and so forth, with non-interference-like transitions between the regions because they are illuminated by different light sources of different non-binary colors in a way that could not occur in a single interference pattern. Periodicity and absolute position of each interference pattern can be independently adjusted by changing positions and tilt angles of mirrors 744 and 746.

Various other interference techniques could be used in an implementation similar to that in FIG. 13. Some examples are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety. Although the technique of FIG. 13 provides a two-color excitation pattern with inter-digitated colors due to different superimposed interference patterns, similar techniques could be used to produce more complex excitation patterns with additional colors, with different arrangements or sizes of regions, and so forth.

Excitation patterns could also be produced in various other ways, including, for example, structured light sources, holography, and so forth. FIGS. 14-18 illustrate several additional ways of obtaining a spatially modulated signal from an object such as a biological cell or virus by a sequence of non-binary excitations between each adjacent pair of which is a non-interference-like transition. In general, the illustrated objects pass through a fluidic or microfluidic channel in which they encounter a sequence of different non-binary excitation regions; depending on the excitation/absorption/scattering spectrum of the object, a time-varying spatially modulated signal is produced, including features that indicate characteristics of the object. For example, if the object is excited by only one of two non-binary excitations, its signal will have different features than if it is excited only by the other or by both of two different non-binary excitations. If the excitations change in a periodic manner, as in FIGS. 9-10 and 13, the resulting signal will also have periodic modulation.

Figure 14:
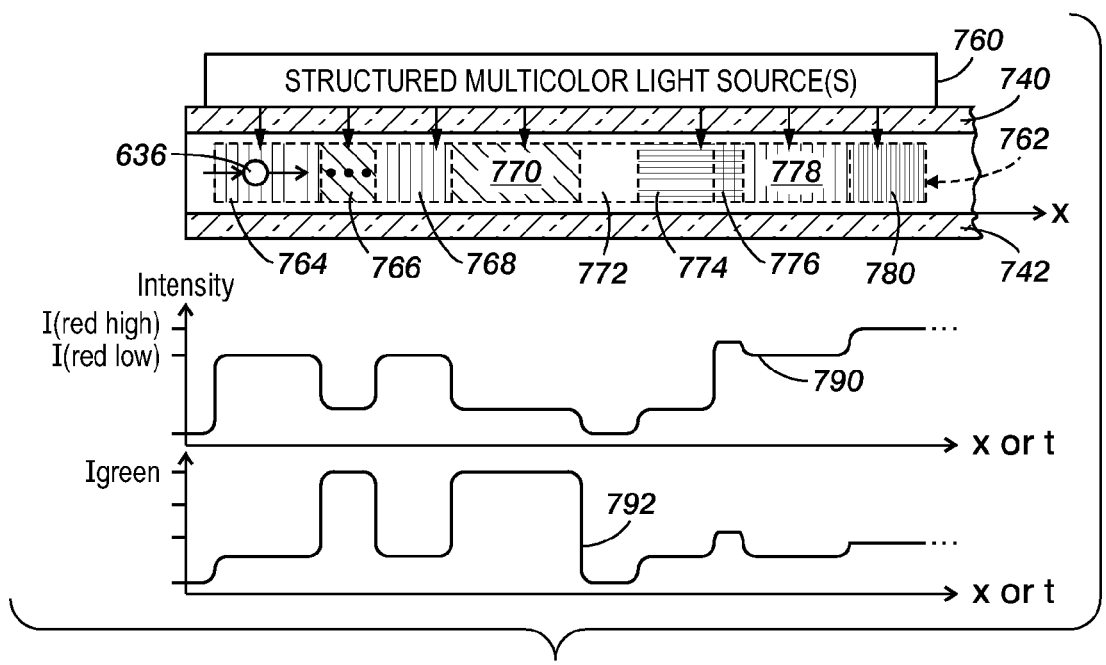
FIG. 14 is a partially schematic cross-sectional view of another excitation arrangement that can be included in an encoding component as in FIG. 2, together with graphs showing emanating intensity for exemplary objects.

FIG. 14 illustrates an example in which object 636, again in a channel between wall-like parts 740 and 742 as in FIG. 13, travels past excitation component 760. Component 760 includes one or more structured multicolored light sources, and produces excitation pattern 762 in the channel. A structured light source could, for example, be active or passive, and could, for example, be implemented with photolithographically structured light emitting diodes (LEDs) or laser diodes (LDs) or even different photolithographically structured phosphors that are excited by a single laser, in which case a large variety of excitation patterns including random patterns could be implemented even with a simple uniform fluidic channel as shown. The minimum feature size (MFS) of the resulting excitation pattern, such as pattern 762, should be of the order of the size of object 636, thereby maintaining a large modulation depth or amplitude of the time-varying signal because each excitation region is relatively short in the longitudinal direction.

Excitation pattern 762 includes a number of types of excitation regions which, taken together, can produce a wide variety of features in a time-varying signal. Excitation regions 764, 766, 768, and 770, for example, illustrate a random two-color pattern of excitation regions between which are non-interference-like transitions, in which the lengths of the regions are not uniform and also are not periodic. After this sequence is region 772, a gap in pattern 762 in which excitation component 760 provides no illumination, thus providing a different type of non-interference-like transition between regions 770 and 774; alternatively, component 760 could provide broadband or white light or any appropriate intermediate intensity in region 772—in any case, the response of objects would be similar to other implementations in which non-colored excitation occurs. While regions 764 and 768 are illustratively red and regions 766 and 770 are illustratively green, region 774 is shown as blue, followed by region 776 in which blue and red excitation overlap, with the overlap providing two other types of non-interference-like transitions that could not occur in a single interference pattern; overlapping excitation regions of this type might provide additional information, e.g because two-photon processes might occur. After overlapping region 776, region 778 provides red excitation at approximately the same level as regions 764 and 768, while region 780 then provides a higher intensity of red excitation, with yet another type of non-interference-like transition between regions 778 and 780; local variations in excitation intensities might allow an even greater variety of non-binary excitation spectra, such as through superimposition of patterns.

Curves 790 and 792 illustrate possible time-varying signals emanating from object 636 as it travels along a path through excitation pattern 762. In the illustrated example, it is assumed that object 636 has a uniform speed or that its actual speed as a function of position has been calibrated with a test pattern, so that the illustrated time-varying signal can also be treated as a position-dependent signal, as indicated by the axis, labeled x OR t. Curve 790 illustrates the signal emanating from an object that responds strongly to red excitation, and much less strongly to blue or green excitation, while curve 792 illustrates an example of an object that responds strongly to green excitation, but only weakly to red or blue excitation. As a result, the parts of curves 790 and 792 from regions 764, 766, 768, and 792 are approximately complementary, with curve 790 being high when curve 792 is low and vice versa; because of the random pattern of excitation, however, ambiguity is avoided—the shapes of curves 790 and 792 can easily be distinguished, even if their amplitudes are similar.

In the illustrated example, curve 790 has an intensity value I(redlow) during regions 764 and 768, while curve 792 has intensity I(green) during regions 766 and 770. Then, in region 772, both curves are approximately at 0, after which each of them rises slightly during region 774 due to blue illumination. In region 776, curve 790 rises slightly above I(redlow), while curve 792 similarly rises due to overlapping excitation. Then, in region 778, curve 790 falls back to I(redlow) while curve 792 returns to the low level it had during regions 764 and 768.

Finally, during region 780, curve 790 rises to I(redhigh), and curve 792 rises slightly from its level during region 778.

In general, the time-varying signals from different types of objects will have different features that make it possible to distinguish the objects, while objects of the same type or the same object on different occasions should produce very similar time-varying signals. More particularly, the modulation depth, sometimes referred to herein as amplitude, of a signal directly indicates its emanation spectrum, as suggested by the difference between curves 790 and 792 across regions 764, 766, 768, and 770.

In the implementations in FIGS. 13 and 14, laminar flow can provide substantially uniform speed. In contrast, FIGS. 15-17 illustrate examples in which laminar flow can produce non-uniform displacement or other variations.

Figure 15:
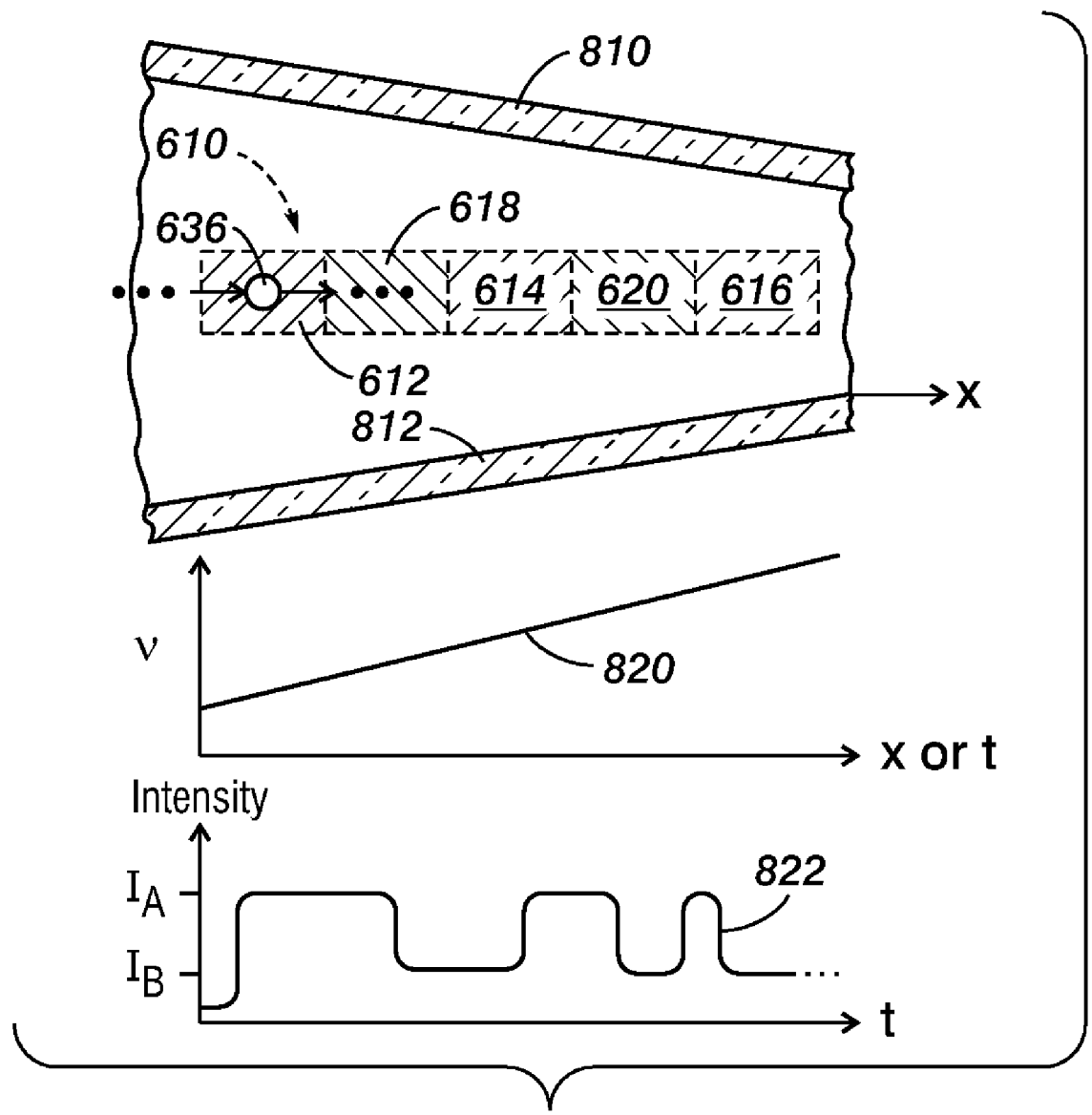
FIG. 15 is another partially schematic cross-sectional view showing a displacement control arrangement that includes shaped boundaries, together with graphs showing velocity of an object and also showing intensity of emanating light as a function of time.

FIG. 15, taken along a line similar to that of FIGS. 13 and 14, shows wall-like parts 810 and 812 with linearly decreasing distance between them. As a result, as object 636 passes through interdigitated two-color excitation pattern 610 with non-interference-like transitions between colors, its velocity increases linearly as indicated by curve 820, either as a function of position or of time. Therefore, rather than a periodic time-varying signal as illustrated in FIG. 10, the resulting time-varying signal is chirped, meaning that the periods decrease linearly due to change in velocity of object 636 resulting from change in flow speed of fluid in the channel as channel dimensions change. Curve 822 illustrates the resulting chirped signal, which has intensity I(A) during regions 612, 614, and 616, and intensity I(B) during regions 618 and 620. As can be seen, the duration of the signal during each successive region is shorter than the preceding region, resulting in the chirped pattern. For the sake of illustration, the linear decrease in transition time is exaggerated in curve 822 in comparison to the narrowing of the channel.

The technique in FIG. 15 is only one of a variety of ways of producing a chirped time-varying signal, and various other techniques could be used. For example, a non-planar mirror such as a spherical mirror could be used to produce a chirped interference pattern analogous to the excitation pattern in FIG. 13, in which case an object would pass through a chirped excitation pattern. Also, more complex flow speed distributions could be obtained by modifying the channel walls in other ways or by providing devices that change the flow speed or flow pattern within the channel, any of which would produce more complex time-varying signals from different objects. In addition, as mentioned above, multicolor interdigitated interference patterns could be used, or excitation patterns could be created with holographic techniques.

Figure 16:
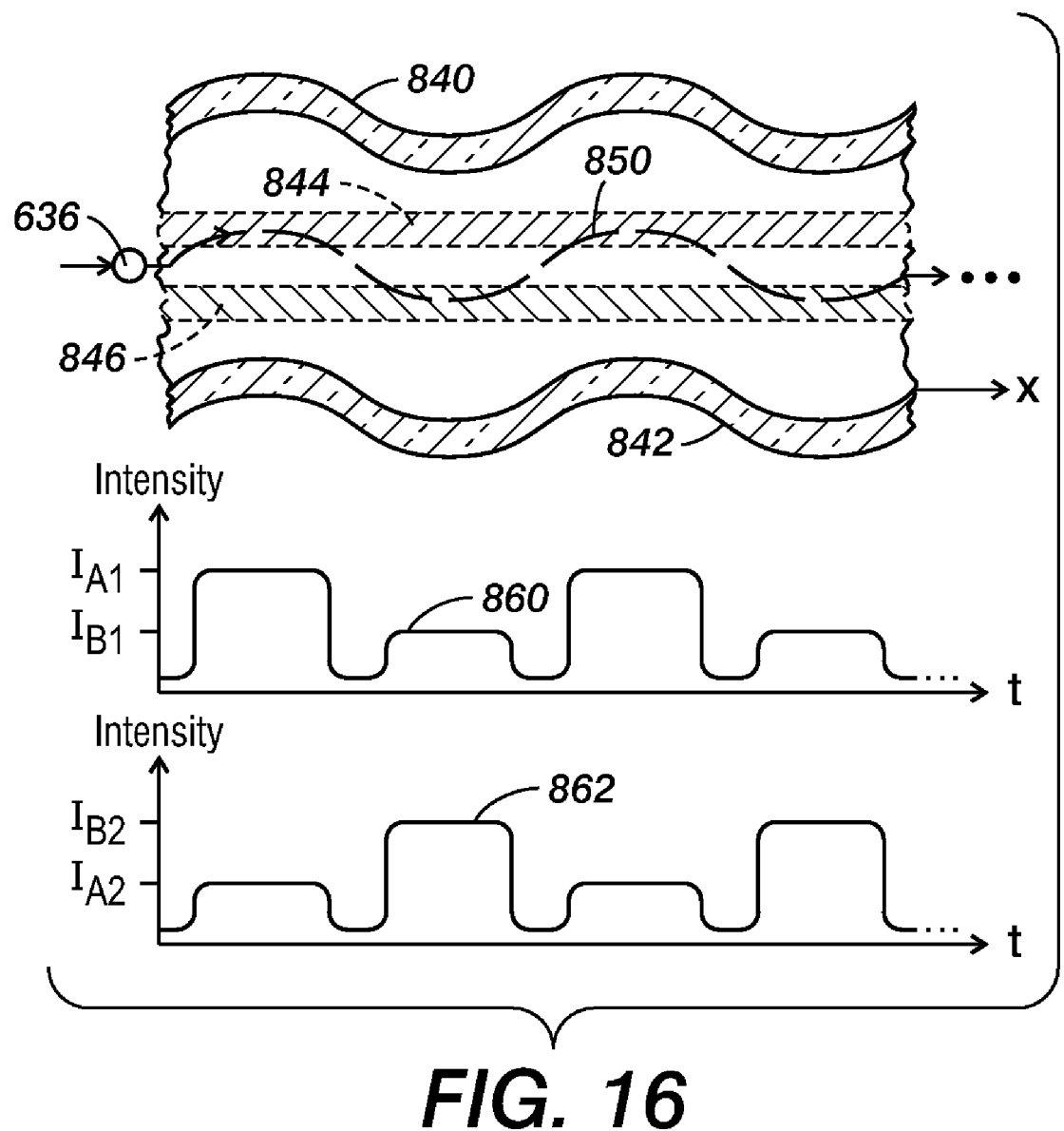
FIG. 16 is a cross-sectional view of another displacement control arrangement that can be included in an encoding component as in FIG. 2, together with graphs showing intensity of emanating light for exemplary types of objects.
Figure 17:
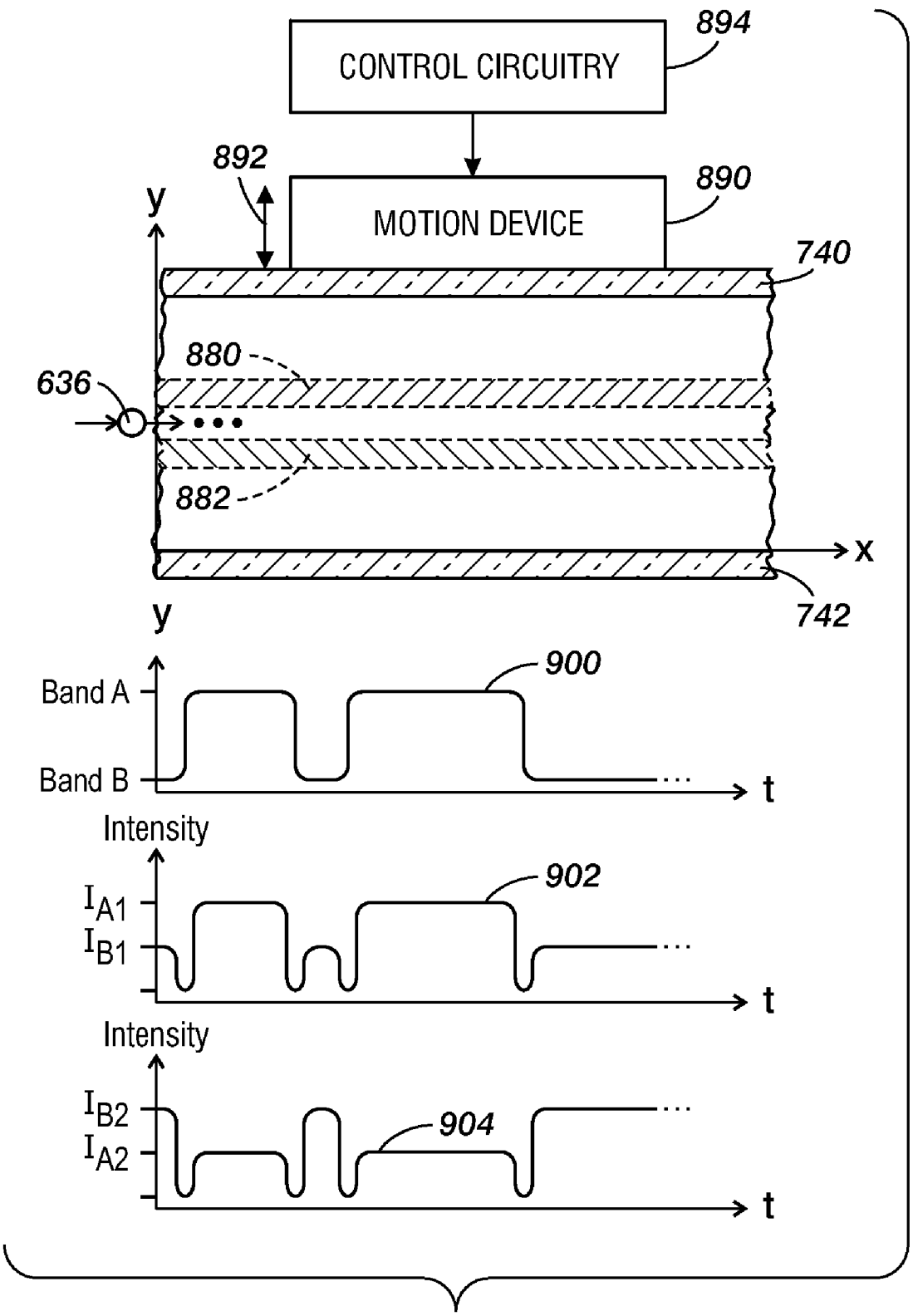
FIG. 17 is a partially schematic cross-sectional view of another displacement control arrangement that can be included in an encoding component as in FIG. 2, together with a graph showing displacement as a function of time and graphs showing intensity of emanating light as a function of time for exemplary types of objects.

FIG. 16 illustrates, on the other hand, how relatively simple time-varying signals could be produced using more complicated techniques. In general, such techniques assume that geometry of a channel directs flow of object 636 in a defined manner such as periodic, chirped, or random, through a sequence of excitation regions. If laminar flow is maintained, as described above, the excitation regions remain undisturbed by channel walls, and can therefore remain homogeneous. This allows redirection of particle flow through a simpler excitation pattern, and may be advantageous in cases where it is easier to redirect particle flow to produce a desired time-variation of emanating light than it would be to produce an excitation source to produce the same time variation; for example, it might be easier to change channel wall shapes than to produce a desired excitation source. In other cases, on the other hand, it might be advantageous to obtain more abrupt or rapid signal transitions with a well-defined excitation source. In addition to the techniques described below, which involve shaping or moving walls, an object's flow within a channel could also be redirected by other techniques; an electrically charged object such as a particle, for example, could be redirected by electrical field variations. In general, however, the Reynolds numbers in typical microfluidic and nanofluidic implementations are so small that laminar flow conditions are, as a practical matter, always present.

In the example in FIG. 16, wall-like parts 840 and 842 are parallel, but each of them is shaped like a sinusoidal wave, resulting in a sinusoidal flow pattern in the channel between them. Excitation regions 844 and 846 are homogeneous of two different colors or gray levels, illustratively labeled "A" and "B". As object 636 follows sinusoidal path 850, it moves back and forth between regions 844 and 846, passing through a small gap between them twice during each period, providing yet another type of non-interference-like transition that would not occur in a single interference pattern. Curves 860 and 862 illustrate exemplary time-varying signals that could result from an object traveling along path 850. Curve 860 illustrates an example of an object of a type that responds strongly to color or gray level A but only weakly to color or gray level B, while curve 862 illustrates an example of an object of a type that responds strongly to color or gray level B and weakly to color or gray level A. As a result, the curves are somewhat complementary, although each curve goes to approximately 0 while path 850 is crossing the gap between regions 844 and 846, during a non-interference-like transition.

Wall-like parts 740 and 742 in FIG. 17 are substantially straight and parallel, as, for example, in FIG. 13. Between them are homogeneous excitation regions 880 and 882, similar to regions 844 and 846 in FIG. 16. Motion device 890, which could be an electrically controlled device such as a solenoid or motor-driven piston, produces relative movement between the path of object 636 and stripe-like regions 880 and 882, as indicated by bi-directional arrow 892. Control circuitry 894 provides signals to control operation of motion device 890; the resulting motion need not be periodic, but could take any appropriate pattern, resulting in arbitrary time-varying signals with features indicating different types of objects. An alternative would be to move the light sources or other components that control positions of regions 880 and 882; more generally, any combination of relative movements between walls 740 and 742 on the one hand and regions 880 and 882 on the other could produce movement as indicated by bidirectional arrow 892. Furthermore, additional variations could be produced by changing fluid flow within the channel so that the speed or other displacement of object 636 changes as a function of time relative to the other movements. Motion device 890 could be set up to produce variations in response to trigger signals indicating incoming objects.

Curve 900 illustrates movement of object 636 in the y-direction between region 880, labeled "Band A", and region 882, labeled "Band B". As illustrated, object 636 spends different lengths of time in each region and can spend a random amount of time in each region, resulting in a random excitation pattern in which non-interference-like transitions occur between the bands. Curves 902 and 904 illustrate exemplary time-varying signals that could be produced by the technique of FIG. 17. One type of object responds more strongly to color or gray level A in region 880, as illustrated by curve 902, while the other responds more strongly to the color or gray level B in region 882, as illustrated by curve 904. As each object travels between regions 880 and 882 and a non-interference-like transition occurs, it passes through the gap between them, resulting in a brief interruption of the emanating light, so that each curve goes briefly to 0. In curve 902, the intensity in region 880 is I(A1), while the intensity in region 882 is I(B1), a lower value. Conversely, curve 904 illustrates that the intensity is higher in region 882, at intensity I(B2), and lower in region 880, at intensity I(A2). The two curves are, in general, complementary, except for times when they are passing through the gap between regions 880 and 882; object 636 can be moved instantaneously between Band A and Band B, moving very quickly across the gap between regions 880 and 882, so that the time in which it is passing through the gap are very brief, though still accompanying a non-interference-like transition between the bands.

Figure 18:
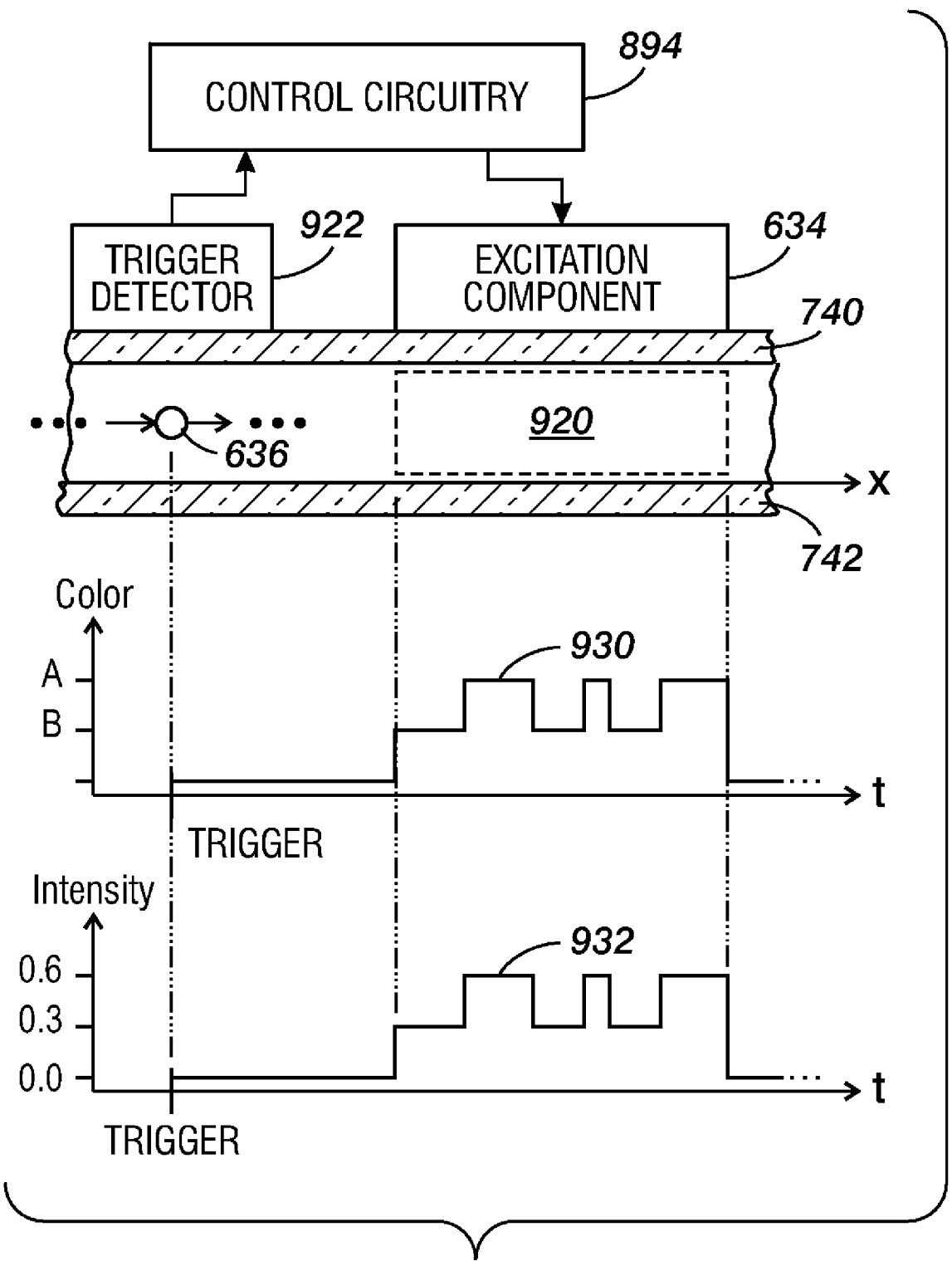
FIG. 18 is a partially schematic cross-sectional view of another excitation arrangement that can be included in the encoding component as in FIG. 2, together with graphs showing color and intensity of excitation as a function of time.

FIG. 18 illustrates a technique in which time-varying signals resulting from different excitation colors or gray levels or even from binary excitations can be produced with a single excitation region in which excitation varies over time, with non-interference-like transitions occurring between intervals during which different excitations are provided. As object 636 travels by laminar flow through the channel between wall-like parts 470 and 472, excitation component 634 is able to produce a sequence of different excitations in excitation region 920. As object 636 passes trigger detector 922, detector 922 provides a trigger signal to control circuitry 924, which can then provide appropriate control signals to excitation component 634. Trigger detector 924 could be implemented, for example, as described in co-pending U.S. patent application Ser. No. 11/315,992, entitled "Sensing Photons From Objects in Channels", incorporated herein by reference in its entirety.

Curve 930 in FIG. 18 illustrates one example of how the color of excitation in region 920 could vary over time, analogous to techniques for varying illumination in a recreational setting such as a dance hall. As shown, excitation of colors A and B alternates, and is provided for random durations, although it could be provided in a periodic or chirp pattern rather than in a random pattern as shown. At each transition between the two colors, a non-interference-like transition occurs because the two different colors would not occur in a single interference pattern. Colors A and B could be non-binary excitation spectra as described above, or could alternatively be black and white. Also, the technique could excite with more than two different colors.

Curve 932 illustrates another example, in which excitation varies between intermediate intensities, such as gray levels, illustratively labeled 0.3 and 0.6 to indicate that they are between minimum intensity of zero and maximum intensity of 1.0. Different intermediate intensities could be provided in this manner with a single light source that can be abruptly switched between intensity levels, providing another type of non-interference-like transitions unavailable from single interference patterns.

In general, accuracy of the technique of FIG. 18 depends on obtaining accurate trigger signals, such as from a Coulter counter or from a backward- or forward-scattered signal, so that time variations are correlated to object positions to produce excitation equivalent to a particular excitation pattern; accuracy also depends on the presence of only one object in region 920 at any given time. The trigger signal from detector 922 can provide additional information about object 636, such as particle size, and this information can be used by control circuitry 924 to select a specific excitation sequence or to scale or otherwise modify a given excitation sequence, such as to optimize information encoded in emanating light; for example, control circuitry 924 could scale the excitation pattern to have a minimum feature size comparable to the dimension of object 636.

Figure 19:
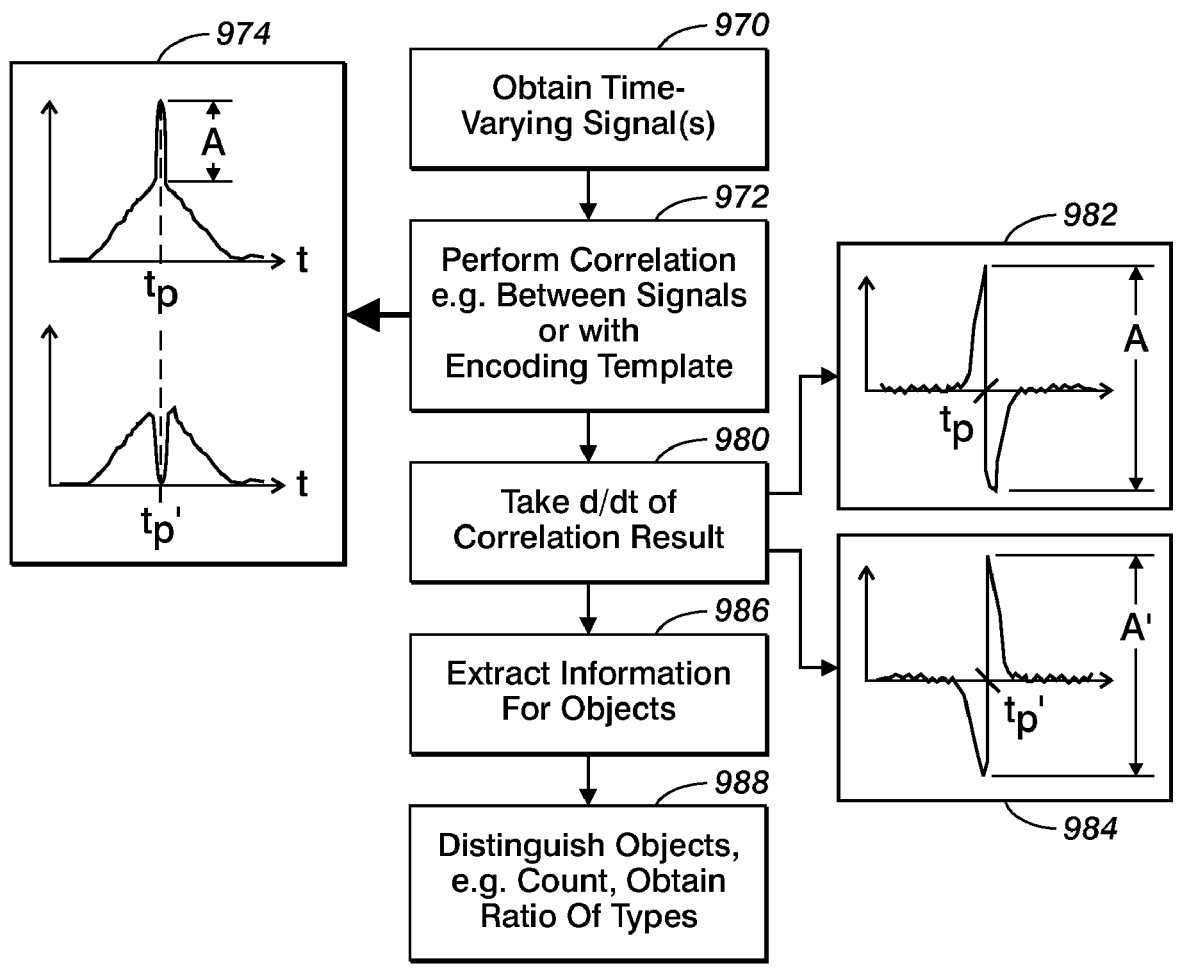
FIG. 19 is a flow chart with graphs illustrating an implementation in which information about objects is obtained from sensed time-varying signals.

The flow chart in FIG. 19 illustrates ways in which information about objects can be obtained and used by CPU 402 (FIG. 6); the technique of FIG. 19 illustratively extracts information such as a type, a position, or a spectral difference, and uses such information to distinguish objects. FIG. 19 also suggests ways in which routines 440, 442, and 444 (FIGS. 6 and 7) could be implemented. Although suitable for CPU 402, operations in FIG. 19 could be implemented with a wide variety of different types of circuitry with or without a CPU. Furthermore, although described in terms of time-varying signals from photosensors, the technique of FIG. 19 could be applied to any time-varying sensed signals, including, for example, capacitively sensed signals from charged particles with encoded information due to shapes, sizes, and positions of electrodes.

The operation in box 970 obtains one or more encoded time-varying signals from a photosensor arrangement as one or more objects travel along respective paths past an excitation arrangement. The technique could be implemented with a single photosensor along the paths, but it might also be possible to implement with two photosensors on opposite sides of the paths or with other photosensor arrangements. The objects can, for example, travel through a channel as described above in relation to FIGS. 8-18 and the time-varying signals can be encoded in any of a wide variety of ways using excitation arrangements, including one or more of those described above, with or without displacement control. For example, if one of the excitation arrangements is at least partially non-periodic or if displacement control or excitation control is at least partially non-periodic, a respective template of the resulting non-periodic pattern for each of a number of types of objects can be used to perform a correlation operation; in other implementations, two differently encoded time-varying signals can be obtained in box 970 and correlated with each other. Note, however, that two types could be distinguished based on a single template, especially if their time-varying signals are sufficiently complementary that one results in correlation and the other in anti-correlation with the template.

The operation in box 970 can include providing any appropriate control signals to other components of the system, including signals to read out sensing results of photosensors. The control signals could be implemented as in routines 440 and 442 (FIG. 6), with CPU 402 providing signals through device I/O 420 to one or more of devices 422 through 424. For example, fluid flow speed could be adjusted, channel wall movement could be controlled, and, in response to trigger signals, excitation components could be controlled as described above in relation to FIG. 18. In order to obtain the time-varying signals, CPU 402 could provide signals through IC I/O 410 to obtain photosensed quantities from ICs 412 through 414.

The operation in box 972 performs a correlation or other comparing operation on one or more time-varying signals from box 970, such as comparing two encoded signals with each other or comparing one encoded signal with a respective template of a non-periodic encoding pattern for each distinguishable type of object. As used herein, the term "correlation operation" encompasses any of a variety of mathematical operations that can be performed on a pair of time-varying functions, with or without scaling, and that obtains a similarity measure as a function of time-alignment. This correlation operation can be implemented, for example, as described in co-pending U.S. patent application Ser. No. 11/698,338, entitled "Method and System for Evaluation of Signals Received from Spatially Modulated Excitation and Emission to Accurately Determine Particle Positions and Distances", incorporated herein by reference in its entirety. Additional correlation and other comparison techniques that could be used are described in co-pending U.S. patent application Ser.

No. 12/022,485 entitled "Obtaining Information from Time Variation of Sensing Results", also incorporated herein by reference in its entirety.

A correlation operation in box 972 can produce correlation results for each pair of waveforms that is compared. For example, if box 972 compares an encoded time-varying signal from box 970 with each of N templates for N types of objects, N correlation results are produced.

The graphed curves in box 974 illustrate two types of correlation results: The upper curve illustrates a correlation result where two time-varying waveforms are correlated, i.e. highly similar at the time alignment designated $t_p$; the lower curve illustrates a correlation result where two time-varying waveforms are anti-correlated, i.e. highly dissimilar at the time alignment designated $t_p'$. In each case there is a peak, with the peak in the correlated case marked to show its amplitude A and with the anti-correlated case having an inverted peak of similar amplitude. If correlation is performed on a continuous basis, correlation results could similarly be continuously obtained for each template with which comparison is made, with each object's travel past the filter arrangement producing a peak, an inverted peak, or a feature in between the two for each template.

The operation in box 980 obtains a time-varying waveform that equals or approximates the time derivative d/dt of each correlation result from box 972. For the correlated case, a derivative waveform like the graphed curve in box 982 is obtained, with a positive peak followed by a negative peak, with a zero crossing at $t_p$, and with the contrast or differential quantity between the peaks again being the amplitude A. For the anti-correlated case, a derivative waveform like the graphed curve in box 984 is obtained, with a negative peak followed by a positive peak, with a zero crossing at $t_p'$, and with the contrast or differential quantity between the peaks being amplitude A', the amplitude of the inverted peak in the lower graph in box 974. The amplitudes obtained in this manner are, in general, free of offsets, allowing direct comparison to obtain spectral information.

The operation in box 986 uses derivative waveforms from box 980 to extract information for objects passing the photosensor. The extracted information could, for example, be a type based on whether an object resulted in correlation, anti-correlation, or neither with a given template; position based on the time at which a zero crossing occurs in correlation or anti-correlation; and spectral difference, e.g. a difference of emission, absorption, or scattering spectrum, based on the amplitude or contrast between positive and negative peaks from correlation and anti-correlation, respectively. The amplitude alone does not reveal a spectral difference between two excitations, for example, where an object emanates light at the same level of intensity for both excitations; the distinction between correlation and anti-correlation, however, can reveal that spectra are in fact different in such cases; spectral difference increases as the difference between intensity levels of emanated light for the two excitations increases. Features of a derivative waveform could be found and measured using various techniques. The operation in box 988 can then be performed to distinguish objects using information extracted in box 986, such as by obtaining counts of different types of objects or ratios between such counts, or with other operations as described above in relation to FIG. 7.

The operations in boxes 972, 980, and 986 could be implemented, for example, as parts of one or both of routines 442 and 444 (FIG. 6). The operation in box 988 could be implemented as part of routine 444. In general, these operations could be implemented to handle signals from each object separately or to handle a signal received concurrently or in series from a number of objects, in which case minimum differences, such as in positions or speeds, may be necessary to allow separation of signals from different objects. Any appropriate combination of serial and parallel operations could be implemented in any appropriate circuitry. Data streams or other data structures defining waveforms such as templates could be stored and retrieved as needed by routines 442 and 444, such as in memory 408 (FIG. 6). Similarly, intermediate and final results of operations in boxes 972, 980, 986, and 988 could similarly be stored and retrieved as needed.

Comparison techniques other than correlation could be employed, but correlation techniques can be advantageous because they are typically not sensitive to noise, such as an AC power frequency. For example, preliminary smoothing or other preprocessing of waveforms is typically unnecessary for correlation, and available techniques for computing correlations can produce useful results even with S/N ratios significantly less than 1.0. It is, however, necessary to satisfy minimum sampling requirements if waveforms are digitized for correlation; in accordance with the Nyquist frequency, each waveform should be sampled at least twice during the time duration of its minimum feature size.

Some techniques as described above have been successfully applied to simulated time-varying waveforms. In particular, time scaling techniques have been found to improve S/N ratio of a simulated observed signal that contains both an encoding based on a template and also additive noise, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few m/sec appear to be feasible, with particles having effective sizes down to 0.6 μm, and with particle separations down to a given implementation's MFS. A demonstration included counting CD4 in a whole blood sample; single tag detection was shown to be feasible.

Where a simulated observed signal includes or is accompanied by a simulated concurrent periodically modulated signal, time scaling of a template waveform based on a scaling factor from the periodically modulated signal has successfully produced matching correlation results, indicating correlation or anti-correlation as appropriate and making spectral information available, in effect allowing concurrent detection of multiple colors with a single detector such as a large-area photosensor. Because an object receives different excitations at almost the same time and location (due, for example, to interdigitated or otherwise patchworked or patterned excitations), differences in absorption and excitation spectra can be measured with very high precision, and many types of errors cancel out, including time-dependent factors such as bleaching, intermixing, diffusion and also errors induced by excitation differences such as temperature gradients and optical misalignments. Particle position can be precisely determined from fine structure of correlation results. As noted above, simulation results show that spatial resolution of less than 1.0 μm is possible, and single fluorescence markers can be detected, making detection possible with smaller amounts of consumables such as markers. The techniques appear appropriate for native fluorescence, allowing agent-less detection.

Some of the implementations described above in relation to FIGS. 1-19 illustrate examples of a method of using an excitation arrangement. While an object travels along a path, the method operates the excitation arrangement to provide excitation within a range of excitation photon energies, and the excitation causes the object to emanate light. In operating the excitation arrangement, the method provides excitation in each of a sequence of segments of the path with a respective non-binary excitation spectrum; the excitation spectra of at least two of the segments are different than each other and have different predominant subranges of the range of excitation energies and/or a non-interference-like transition between them. In response to the different excitation spectra, the object emanates light differently so that, while it travels along a part of the path that includes the sequence, the emanating light has time variation.

In specific implementations, the method can also include photosensing a portion of the emanating light from the object. In addition, the photosensing results can include information about the object that was encoded in time variation of the emanating light. The photosensing results can include one or more sensed time-varying signals. In using the photosensing results, the method can perform a comparing operation between two time-varying signals to obtain comparison results, with at least one being a sensed time-varying signal, and can use the comparison results to obtain data indicating a spectral difference between the two time-varying signals.

In further specific implementations, the object can be fluorescent, fluorescing at different intensities in response to the different excitation spectra. The excitation spectra of at least two of the segments can have different predominant subranges of the range of excitation energies and/or can have different intermediate intensities; the spectra can be gray levels that have different intermediate intensities, for example.

In further specific implementations, the method can provide an excitation pattern that includes two or more excitation regions with a non-interference-like transition between them, with the object traveling through a respective excitation region in each segment. The method can provide the excitation pattern by operating a structured multi-color light source. The excitation pattern can include two interdigitated interference patterns, provided from two light sources with different predominant photon energies, and with adjacent regions in the interdigitated patterns having a non-interference-like transition between them.

In further specific implementations, the excitation pattern can be substantially continuous, the object crossing a non-interference-like transition in moving from a preceding segment's excitation region to the following segment's excitation region, and with the excitation regions in a longitudinal sequence that is a random, periodic, or chirped sequence, e.g. a periodic sequence of two alternating colors. The pattern can include a gap between regions, and an object can cross the gap during a non-interference-like transition, in traveling from one segment to another. The object's velocity can be caused to change linearly as it travels through the part of the path, and the emanating light can include chirped time variation. While operating the excitation arrangement, the method can cause the object to move through a channel with a boundary shape that causes the object to travel on a non-straight line; the boundary can have a sinusoidal shape, and the excitation regions can be stripe-like regions that are approximately parallel to the path or in a lengthwise direction, in which case the method can cause relative movement between the object and the excitation pattern in a direction not parallel to the lengthwise direction. In general, relative movement can be non-periodic.

In further specific implementations, the method can provide time-varying excitation while the object travels through the part of the path, and the time-varying excitation can include excitation intervals during which the excitation has different non-binary excitation spectra. A non-interference-like spectral transition can occur between the excitation intervals. The excitation intervals can, for example, have different predominant photon energy subranges. The object can travel through each of the segments during a respective excitation interval. In general, the time-varying excitation can be non-periodic.

In further specific implementations, each of the segments in the sequence can be at least approximately as large as the object's size.

Some of the implementations described above in relation to FIGS. 1-19 illustrate examples of a method similar to that described above in which objects travel past the excitation arrangement, with the objects emanating light differently in response to the different excitation spectra and the emanating light therefore having time variation. In specific implementations, the method can also include photosensing a portion of the emanating light from the objects and obtaining photosensing results, which can be used to distinguish objects, such as in a series. In further specific implementations, the method can encode information about objects in time variation of each object's emanating light.

Some of the exemplary implementations described above in relation to FIGS. 1-19 also illustrate examples of apparatus (or a system) that includes a fluidic structure and an encoding component. The fluidic structure includes a channel through which objects can travel along respective paths during operation. The encoding component includes an excitation arrangement that can provide excitation as described above.

In specific implementations, the apparatus can also include a photosensing component that photosenses the emanating light and provides photosensing results, and a processing component that performs operations on the photosensing results to obtain signals indicating information encoded in the emanating light. The photosensing results can include one or more sensed time-varying signals. The processing component can be programmed to perform a comparing operation and use the comparison results as described above.

In further specific implementations, the excitation arrangement can include first and second light sources that provide first and second interference patterns in first and second predominant photon energies, respectively, and optical components that provide the first and second interference patterns in an interdigitated pattern in the channel. In other specific implementations, the excitation arrangement can include a structured multi-color light source that provides an excitation pattern. The channel can have boundaries shaped to cause each object to travel with non-uniform displacement, such as change of displacement rate and/or change of displacement direction. The apparatus can also include a device that can cause relative motion between the objects and an excitation pattern.

In further specific implementations, the apparatus can also include a trigger detector along the channel that responds to each object, providing a respective trigger signal. The apparatus can also include circuitry that responds to the trigger signal, causing the excitation arrangement to provide time-varying excitation while the object travels through the part of its path, and the time-varying excitation can include two or more excitation intervals during which it provides different excitation spectra. The excitation spectra can include non-binary spectra and there can be a non-interference-like transition between excitations. The object can travel through each segment during a respective excitation interval.

In specific implementations, the objects can be biological cells or viruses. The apparatus can be a flow cytometer.

Some of the exemplary implementations described above in relation to FIGS. 1-19 illustrate examples of apparatus (or a system) that includes a fluidic structure as described above and an encoding component with an excitation source, a trigger detector, and circuitry. The excitation source can provide excitation to objects in an excitation region of the channel, causing the objects to emanate light, and the excitation source is capable of providing at least two different excitation spectra. The trigger detector is along the channel upstream from the excitation region, and responds to each object by providing a respective trigger signal. The circuitry responds to each object's trigger signal, causing the excitation source to provide time-varying excitation while the object travels through the excitation region. The time-varying excitation includes two or more excitation intervals during each of which the excitation source provides different excitation spectra.

In specific implementations, the excitation source can provide the excitation intervals with a non-interference-like transition between them. The excitation spectra can be non-binary. The time-varying excitation can include at least one of a periodic, random, and chirped sequence of excitation intervals.

Implementations as described above in relation to FIGS. 1-19 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g. tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Implementations described above could successfully detect native fluorescence differences between biological materials. Most biological cells are composed of only a few basic building blocks and, therefore, exhibit similar native fluorescence spectra. Spatially modulated excitation techniques like those above are particular suitable for differentiation of objects based on their native fluorescence signals because the techniques are sensitive enough to detect the native fluorescence from a single cell and allow direct measurement of distinguishing features such as intensity ratios in emission or excitation spectra. In addition, implementations of the techniques can combine advantages of excitation and emission spectroscopy in a rugged and compact system.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Exemplary implementations described above employ photosensors or impedance-based sensors with specific features, but a wide variety of sensors could be used to obtain sensing results indicating values of various parameters other than emanating light intensity, parameters that can have time variation that indicates information about objects. Similarly, implementations described above involve sensing information about objects that are moving in fluidic channels or that are moving relative to a sensor such as in scanning, but various other types of fluidic implementations or other implementations in which objects move in various other ways could be sensed to obtain sensing results suitable for techniques described above. For example, information could be obtained from native fluorescence of particles in an air stream. Also, an excitation pattern could be scanned across a glass slide with immobilized analyte particles such as tagged cells or DNA spots, to obtain emanating fluorescent light.

Components of exemplary implementations as described above could have various shapes, dimensions, or other numerical or qualitative characteristics other than those illustrated and described above. Similarly, although the exemplary implementations generally involve sensing from a single fluidic channel, implementations could readily include multiple parallel channels, allowing parallel sensing and readout and larger scale sensing.

Some of the above exemplary implementations involve specific types of fluidic components, filter components, light source components, displacement control components, sensors, and so forth, but the invention could be implemented with a wide variety of other types of components. For example, some implementations use specific types of spatial modulation based on one or more of an excitation pattern, a filter assembly, and/or displacement control, but various other types of spatial modulation could be used, including any appropriate combination of color, gray level, and black and white patterning and including other patterning techniques such as patterned sensing; for example, in a fluidic implementation, a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; either or both of two compared waveforms could be obtained in analog or digital form, and any combination of time scaling could be performed before comparison. Further, some exemplary implementations use large area photosensors, but various ICs with photosensing arrays might be used.

Some of the above exemplary implementations involve specific types of emanating light, e.g. fluorescence, and specific types of excitation and filtering suitable to fluorescent light, but these are merely exemplary. The invention could be implemented in relation to various other types of optical signals in various other ranges of photon energies or with any other appropriate sensed stimuli.

Some of the above exemplary implementations involve specific fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 6 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing arrangements, sensors, photosensors, excitation arrangements, filter arrangements, displacement control arrangements, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell or in a streaming operation. Principal component analysis could be applied to specifically chosen absorption ratios in distinguishing cells or other objects, possibly allowing identification. Multiple photosensors along a channel could measure different absorption ratios, possibly allowing identification of objects based on either absorption or excitation characteristics. Dyes that are very similar may be distinguishable if they reveal different absorption values at excitation wavelengths, and use of similar dyes could be advantageous in satisfying pH requirements within cytometers.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of using an excitation arrangement, the method comprising:
   while an object travels along a path, operating the excitation arrangement to provide excitation to the object within a range of excitation photon energies, the excitation causing the object to emanate light; the act of operating the excitation arrangement including:
   in each of a sequence of segments of the path, providing an excitation pattern with a respective non-binary excitation spectrum within the range of excitation energies, the respective excitation spectra of at least two of the segments being different than each other and including:
   a non-interference-like transition between the at least two segments;
   in response to the different excitation spectra, the object emanating light differently so that, while the object travels along a part of the path that includes the sequence of segments, the emanating light has time variation.

2. The method of claim 1 in which the act of operating the excitation arrangement further includes:
   providing an excitation pattern that includes two or more excitation regions with a non-interference-like transition between excitation regions; in each of the at least two segments, the object traveling through a respective excitation region in the excitation pattern.

3. The method of claim 2 in which the excitation pattern is substantially continuous so that, when an object travels from a preceding segment in the sequence to the preceding segment's following segment, the object crosses a non-interference-like transition in moving from the preceding segment's excitation region to the following segment's excitation region; the excitation regions being a longitudinal sequence within the excitation pattern, the longitudinal sequence being one of:
   a random sequence;
   a periodic sequence; and
   a chirped sequence.

4. The method of claim 2 in which the method further comprises, while operating the excitation arrangement:
   causing the object to move through a channel with a boundary shape that causes the object to travel on a non-straight line.

5. The method of claim 4 in which the channel's boundary has a sinusoidal shape, the excitation regions being stripe-like regions that are approximately parallel to the path.

6. The method of claim 4 in which the excitation regions are stripe-like regions extending in a lengthwise direction, the act of causing the object to move comprising:
   causing relative movement between the object and the excitation pattern in a direction not parallel to the lengthwise direction.

7. The method of claim 1 in which the act of operating the excitation arrangement further includes:
   providing time-varying excitation while the object travels through the part of the path, the time-varying excitation including two or more excitation intervals during which the excitation has different non-binary excitation spectra and between which is a non-interference-like transition; the object traveling through each of the at least two segments during a respective one of the excitation intervals.

8. A method of using an excitation arrangement, the method comprising:
   while objects travel past the excitation arrangement, operating the excitation arrangement to provide excitation to the objects within a range of excitation photon energies, the excitation causing the objects to emanate light; the act of operating the excitation arrangement including:
   providing an excitation pattern that includes two or more excitation regions, each with a respective non-binary excitation spectrum within the range of excitation energies; each of the objects traveling through a sequence of the excitation regions that includes at least two regions whose excitation spectra are different than each other and including
   a non-interference-like transition between the at least two regions;
   in response to the different excitation spectra, each object emanating light differently so that, while the object travels through the sequence of excitation regions, its emanating light has time variation.

9. Apparatus comprising:
   a fluidic structure that includes a channel through which objects can travel along respective paths during operation of the apparatus; and
   an encoding component; the encoding component including
   an excitation arrangement that can provide excitation to objects in the channel within a range of photon energies, the excitation causing the objects to emanate light; the excitation arrangement providing the excitation so that each object's path includes a sequence of segments in each of which the excitation arrangement provides excitation with a respective non-binary excitation spectrum within the range of photon energies, the respective excitation spectra of at least two of the segments being different than each other and including a non-interference-like transition between the at least two of the segments;

in response to the different excitation spectra, each object emanating light differently so that, while the object travels along a part of its path that includes the at least two segments, the emanating light has time variation.

10. The apparatus of claim 9, further comprising:

a photosensing component that photosenses the emanating light of the objects and provides photosensing results; the photosensing results including one or more sensed time-varying signals; and a processing component that performs operations on the photosensing results to obtain signals indicating information encoded in the emanating light the processing component being programmed to:

perform a comparing operation between two time-varying signals to obtain comparison results, at least one of the time-varying signals being one of the sensed time-varying signals; and use the comparison results to obtain data indicating at least one spectral difference between the two time-varying signals.

11. The apparatus of claim 9 in which the excitation arrangement comprises:

first and second light sources that provide first and second interference patterns in first and second predominant photon energy subranges in the range of photon energies, respectively; and optical components that provide the first and second interference patterns in an interdigitated pattern in the channel.

12. The apparatus of claim 9 in which the excitation arrangement comprises:

a structured multicolor light source that provides an excitation pattern.

13. The apparatus of claim 9 in which the channel has boundaries shaped to cause each object to travel along its path with non-uniform displacement.

14. The apparatus of claim 9 in which the apparatus further comprises:

a device that can cause relative motion between the objects and an excitation pattern.

15. The apparatus of claim 9 in which the excitation arrangement includes an excitation component that operates as one side of the channel.

16. Apparatus comprising:

a fluidic structure that includes a channel through which objects can travel along respective paths during operation of the apparatus; and an encoding component that includes:

an excitation source that can provide excitation to objects in an excitation region of the channel within a range of photon energies, the excitation causing the objects to emanate light; the excitation source being capable of providing at least two different excitation spectra within the range of photon energies;

a trigger detector along the channel upstream from the excitation region, the trigger detector responding to each of the objects as it passes, providing a respective trigger signal; and circuitry that responds to each object's trigger signal, causing the excitation source to provide time-varying excitation while the object travels through the excitation region, the time-varying excitation including two or more excitation intervals during each of which the excitation source provides different ones of the excitation spectra.

17. The apparatus of claim 16 in which the excitation spectra are non-binary excitation spectra.

18. The apparatus of claim 16 in which the time-varying excitation includes at least one of:

a periodic sequence of excitation intervals;

a random sequence of excitation intervals; and a chirped sequence of excitation intervals.

19. A method of using an excitation arrangement, the method comprising:

while an object travels along a path, operating the excitation arrangement to provide excitation to the object within a range of photon energies, the excitation causing the object to emanate light; the act of operating the excitation arrangement including:

in each of a sequence of segments of the path, providing respective excitation with a respective non-binary excitation spectrum within the range of photon energies;

successive segments in the sequence having respective excitation spectra sufficiently different that the object emanates light differently in the successive segments and, while the object travels along a part of the path that includes the sequence of segments, its emanating light has time variation; and providing respective excitation of each segment in the sequence through a respective path length so that the sequence includes a substantially continuous spatial pattern of excitation, the spatial pattern including at least one of:

a non-periodic pattern;

a periodic pattern; and a chirped pattern;

the time variation of the object's emanating light including, as a result of the spatial pattern, at least one of:

non-periodic time variation;

periodic time variation; and chirped time variation.

20. The method of claim 19 in which the object is fluorescent, the object fluorescing at different intensities in response to the different excitation spectra.

21. The method of claim 19 in which the respective excitation spectra of at least two of the segments have different predominant subranges of the range of photon energies and/or have different intermediate intensities.

22. The method of claim 19 in which the respective excitation spectra are gray levels that have different intermediate intensities.

23. The method of claim 19 in which the act of providing respective excitation of each segment includes:

operating a structured multicolor light source to provide the spatial pattern.

24. The method of claim 19, further comprising:

causing the object's velocity to change linearly as the object travels through the part of the path, the emanating light from the object including chirped time variation.

25. The method of claim 19 in which the spatial pattern includes two interdigitated interference patterns, the act of operating the excitation arrangement further including:

providing the interdigitated interference patterns from two light sources that provide light with different predominant photon energies in the range of photon energies.

26. The method of claim 19, further comprising:
photosensing a portion of the emanating light from the object and obtaining photosensing results; the photosensing results including one or more sensed time-varying signals; and
using the photosensing results to obtain information about the object; the act of using the photosensing results including:
performing a comparing operation between two time-varying signals to obtain comparison results, at least one of the time-varying signals being one of the sensed time-varying signals; and
using the comparison results to obtain data indicating at least one spectral difference between the two time-varying signals.

27. A method of using an excitation component, the method comprising:
while an object travels through a region, operating the excitation component to provide excitation in the region within a range of photon energies, the excitation causing the object to emanate light; the act of operating the excitation component including:
during each of a sequence of intervals, providing respective excitation with a respective excitation spectrum within the range of photon energies; the respective excitation spectra of successive intervals in the sequence being sufficiently different that the object emanates light differently during the successive intervals and, during the sequence of intervals, its emanating light has time variation; and
providing respective excitation of each interval in the sequence during a respective duration so that the sequence includes a substantially continuous pattern of excitation over time, the pattern of excitation over time including at least one of:
a non-periodic pattern;
a periodic pattern; and
a chirped pattern;
the time variation of the object's emanating light including, as a result of the pattern of excitation over time, at least one of
non-periodic time variation;
periodic time variation; and
chirped time variation.

28. The method of claim 17 in which time variations of the object's emanating light are correlated with the object's position in the region and, while the object travels through the region, it is the only object in the region that is emanating light in response to the pattern of excitation over time.

29. A method of using an excitation arrangement, the method comprising:
while objects travel past the excitation arrangement, operating the excitation arrangement to provide excitation to the objects within a range of photon energies, the excitation causing each object to emanate light in accordance with a respective emanation spectrum, the respective emanation spectra of at least some objects being different; the act of operating the excitation arrangement including:
providing a substantially continuous excitation pattern, the excitation pattern including at least one of:
a non-periodic pattern;
a periodic pattern; and
a chirped pattern; and
the excitation pattern further including one of:
a longitudinal sequence of segments, each with respective excitation having a respective non-binary excitation spectrum within the range of photon energies; successive segments in the longitudinal sequence having respective excitation spectra sufficiently different that objects with different emanation spectra emanate light differently in the successive segments and, while an object travels through the longitudinal sequence of segments, its emanating light has respective time variation that encodes information about the object's emanation spectrum; and
a time sequence of intervals, each with respective excitation having a respective excitation spectrum within the range of photon energies; the respective excitation spectra of successive intervals in the time sequence being sufficiently different that objects with different emanation spectra emanate light differently during the successive intervals and, during the time sequence, an object's emanating light has respective time variation that encodes information about the object's emanation spectrum; and
distinguishing at least one of the objects based on the information about the object's emanation spectrum encoded in the respective time variation.

30. The method of claim 29 in which the act of distinguishing at least one of the objects includes:
photosensing a portion of the emanating light from the objects and obtaining photosensing results; and
using the photosensing results to distinguish objects.

31. The method of claim 29 in which the objects include objects of first and second types that have first and second emanation spectra, respectively, the first and second emanation spectra being different from each other; the act of distinguishing at least one of the objects including:
distinguishing objects of the first and second types from each other based on the information about each object's emanation spectrum encoded in the respective time variation.

32. The method of claim 31 in which the act of distinguishing objects of the first and second types includes:
photosensing a portion of each object's emanating light and obtaining respective photosensing results; each object's photosensing results including a respective sensed time-varying waveform; objects of the first and second types having respective sensed time-varying waveforms with parts that are approximately complementary to each other.

33. The method of claim 32 in which the excitation pattern includes at least one of:
a periodic pattern with a duty cycle different from 0.5; and
a non-periodic pattern.

* * * * *